US011492377B2

(12) United States Patent
Prangsgaard

(10) Patent No.: US 11,492,377 B2
(45) Date of Patent: Nov. 8, 2022

(54) PARVOVIRUS STRUCTURAL PROTEIN FOR THE TREATMENT OF AUTOIMMUNE DISEASES

(71) Applicant: 2A PHARMA AB, Malmo (SE)

(72) Inventor: Jeanette Prangsgaard, Aalborg Öst (DK)

(73) Assignee: 2A PHARMA AB, Malmo (SE)

( * ) Notice: Subject to any disclaimer, the term of this patent is extended or adjusted under 35 U.S.C. 154(b) by 201 days.

(21) Appl. No.: 16/969,141

(22) PCT Filed: Feb. 14, 2019

(86) PCT No.: PCT/EP2019/053649
§ 371 (c)(1),
(2) Date: Aug. 11, 2020

(87) PCT Pub. No.: WO2019/158636
PCT Pub. Date: Aug. 22, 2019

(65) Prior Publication Data
US 2021/0040157 A1 Feb. 11, 2021

(30) Foreign Application Priority Data

Feb. 16, 2018 (EP) .................................... 18157083
Jun. 11, 2018 (EP) .................................... 18176976

(51) Int. Cl.
A61K 39/00 (2006.01)
A61K 39/12 (2006.01)
C07K 14/005 (2006.01)
C12N 15/86 (2006.01)
A61K 39/39 (2006.01)
A61P 37/06 (2006.01)
A61P 17/00 (2006.01)

(52) U.S. Cl.
CPC ............ *C07K 14/005* (2013.01); *A61P 17/00* (2018.01); *A61P 37/06* (2018.01); *C12N 2750/14322* (2013.01)

(58) Field of Classification Search
CPC . A61P 35/00; A61K 2039/53; A61K 39/0011; A61K 39/12; C07K 14/005
See application file for complete search history.

(56) References Cited

FOREIGN PATENT DOCUMENTS

| WO | WO2008145400 | * | 12/2008 |
|---|---|---|---|
| WO | WO2008145400 A2 | | 12/2008 |
| WO | WO2012031760 A1 | | 3/2012 |
| WO | WO2013033395 A1 | | 3/2013 |

OTHER PUBLICATIONS

International Search Report and Written Opinion dated Apr. 5, 2019 in International Application No. PCT/EP2019/053649, 12 pages.
Mazano-Szalai et al., "Adeno-associated virus-like particles as new carriers for B-cell vaccines: Testing immunogencity and safety in BALB/c mice," Nov. 2014, Viral Immunology, 27(9): 438-448.
Singer et al. "Proof of concept study with an HER-2 mimotype anticancer vaccine deduced from a novel AAV-mimotype library platform," Apr. 2016, OncoImmunology, 5:7, e1171446, 12 pages.

* cited by examiner

*Primary Examiner* — Barry A Chestnut
(74) *Attorney, Agent, or Firm* — Lee & Hayes, P.C.

(57) ABSTRACT

The present invention relates to a mutated parvovirus structural protein, comprising at least one insertion comprising a sequence of at least six consecutive amino acids comprised within amino acids 320 to 641 of human HSP70i. Furthermore, the invention relates to multimeric structures comprising the protein, VLPs, a method of producing the mutated parvovirus structural protein and to medicaments or vaccines comprising the mutated parvovirus structural protein that may be used for treating vitiligo or other autoimmune diseases.

18 Claims, 5 Drawing Sheets

Specification includes a Sequence Listing.

PARVOVIRUS STRUCTURAL PROTEIN FOR THE TREATMENT OF AUTOIMMUNE DISEASES

CROSS REFERENCE TO RELATED APPLICATIONS

This application is a U.S. National Phase Application of International Application No. PCT/EP2019/053649, filed Feb. 14, 2019, which claims priority to European Application EP 18176976.1, filed Jun. 11, 2018, and European Application No. EP 18157083.9, filed Feb. 16, 2018, all of which are hereby incorporated by reference in their entirety.

FIELD OF INVENTION

The present invention relates to a mutated parvovirus structural protein, comprising at least one insertion comprising a sequence of at least six consecutive amino acids comprised within amino acids 320 to 641 of human HSP70i. Furthermore, the invention relates to multimeric structures comprising the protein, VLPs, a method of producing the mutated parvovirus structural protein and to medicaments or vaccines comprising the mutated parvovirus structural protein that may be used for treating vitiligo or other autoimmune diseases.

BACKGROUND

Vitiligo is the most frequently occurring depigmentary disorder affecting approximately 0.5 to 2% of the population worldwide. Vitiligo lesions are milky white patches that can increase in shape and size and may affect most parts of the body. The disease may develop at any age. However, half of the patients are affected by vitiligo before the age of 20 years. Vitiligo has been shown to exert a detrimental influence on the quality of life, mainly due to the change in appearance of the patients caused by the depigmentation. The disorder can affect the patients' emotional and psychological well-being. Vitiligo is associated with an increased risk of developing a depression, and more than a third of the patients with vitiligo experience some type of depressive symptoms without necessarily fulfilling all criteria for clinical depression (Speeckaert & van Geel, 2017).

Vitiligo can be differentiated into the far more common form of non-segmental vitiligo and segmental vitiligo. Non-segmental vitiligo is characterized by the development of depigmentation on both sides of the body, whereas segmental vitiligo is limited to one side of the body, usually not crossing the midline of the body. Non-segmental vitiligo usually has a chronic course with a continuing progression throughout life. In contrast, segmental vitiligo is characterized by a rapid disease onset and a disease stabilization after one to two years. Early recognition of the vitiligo subtype is essential, as the treatment is markedly different (Speeckaert & van Geel, 2017).

At present, topical corticosteroids are the established first-line treatment option for the management of vitiligo. The anti-inflammatory effects of these compounds might decrease disease progression. However, their effect on repigmentation is limited. Generally, most repigmentation can be observed in the face and neck, while only limited repigmentation is observed on the trunk, extremities and especially the hands. The side effects of corticosteroids include skin atrophy, telangiectasia and striae. Treatment is often continued for at least six months, with the primary aim to achieve a disease stabilization. As an alternative to a topical administration, corticosteroids may be administered orally at moderate doses. Oral corticosteroid therapy has been shown to stop disease progression in the majority of the patients. However, also for orally administered corticosteroids, repigmentation is only rarely observed. Furthermore, oral corticosteroid administration is associated with a variety of side effects, such as weight gain, acne, sleep disturbances, agitation, hypertrichosis and menstrual abnormalities which limit long-term use. Alternative to corticosteroids, a topical treatment of vitiligo may be based on topical immune modulators, such as tacrolimus or pimecrolimus, which attenuate T-cell activity. Similar to corticosteroids, the treatment shows most repigmentation in the face, while the results are moderate at other sides of the boy. Side effects include a burning sensation or flushing after alcohol intake, which is often observed and can be bothersome for some patients (Speeckaert & van Geel, 2017).

In addition to pharmacological treatments, phototherapy, especially narrow-band UVB phototherapy, has been established as a treatment for vitiligo. Phototherapy shows signs of repigmentation in the majority of the patients, however, complete repigmentation is only found in a minority of patients. Additionally, a relapse after discontinuation of phototherapy is frequently observed (Speeckaert & van Geel, 2017). In summary, the established therapies for vitiligo have a limited efficacy, are frequently associated with side effects, and usually have to be administered over a prolonged period of time, such as weeks or months.

Based on the observation that expanding vitiligo lesions are frequently infiltrated by cytotoxic T-cells directed against melanocyte differentiation antigens, such as Mart-1 or GP100, vitiligo is considered as an autoimmune disease. It has further been shown that psychological as well as chemical or mechanical stress contributes to the autoimmune aetiology of the vitiligo (Mosenson et al., 2013; Speeckaert & van Geel, 2017). Accordingly, the involvement of heat-shock proteins (HSP), especially of the inducible isoform of HSP70 (HSPi), in the cellular mechanisms underlying vitiligo has been examined. Human HSP70i is also known as HSP70A1A or HSP70A1B, which are characterized by the same amino acid sequence, but are yet encoded by separate genes with different regulatory regions. HSP70i is generally considered as a cytoplasmic protein, similar to HSC70, but is also secreted by living cells in contrast to the other members of the HSP70 protein family (Mosenson et al., 2013). HSP70 family proteins are known to be involved in the activation and maturation of dendritic cells (DCs), in the antigen presentation by the DCs and in the activation of T-cells. HSP70 contributes to the process of antigen presentation by dendritic cells by a) forming a complex with a peptide antigen, b) delivering the peptide to the antigen-presenting cell and transferring the peptide into the cell, c) intracellularly chaperoning the antigen for MHC class I presentation. On the surface of the antigen-presenting cell, the HSP70-antigen complex may either bind to signaling receptors, such as TLR2, TLR4 and CD91 or to scavenger receptors, such as LOX-1, SREC-1, FEEL-1/CLEVER-1 or CD91. Binding of the HSP-antigen complex to signaling receptors may activate the cytokine production of the antigen-presenting cells, whereas binding to scavenger receptors results in receptor-mediated endocytosis of the complex. This stimulatory effect of HSP70 is mediated by the C-terminal domain of the protein (Malyshev, 2013).

As shown by Mosenson et al., HSP70i is expressed at significantly higher levels in the lesional or perilesional skin in comparison to non-lesional skin. Furthermore, vitiligo melanocytes secreted significantly more HSP70i in response to oxidative stress, in comparison to control melanocytes in agreement with the assumed stress-related function of HSP70i in the autoimmune aetiology of vitiligo (Mosenson et al., 2014).

The role of HSP70i in vitiligo was also confirmed by different animal models. It could, for example, be shown that vaccination of mice with a eukaryotic expression plasmid encoding the melanocyte differentiation antigen TRP-2 significantly increased depigmentation when administered in combination with a plasmid encoding HSP70i, whereas vaccination with a plasmid encoding only the melanocyte differentiation antigen alone increased depigmentation to a significantly lower extent. Notably, the effect of HSP70i was not diminished by HSP70i antibodies expressed in response to the vaccination (Denman et al., 2009). A significantly increased depigmentation was also observed in mice vaccinated with a plasmid encoding TRP-2 in combination with a plasmid encoding the C-terminal region (amino acids 320 to 641) of HSP70i. In contrast thereto, depigmentation was hardly increased upon vaccination with a plasmid encoding TRP-2 in combination with a plasmid encoding the N-terminal region (amino acids 1 to 377) of HSP70i (Mosenson et al., 2013).

Within the C-terminal region of HSP70i, the peptide sequence QPGVLIQVYEGER seems to be required for the activation of dendritic cells. The respective sequence is homologous to the DnaK peptide QPSVQIQVYQGEREIAAHNK (DnaK amino acids 407 to 426) which is known to drive dendritic cell activation during inflammation in response to infection. HSP70i variants comprising the amino acid exchange Q435A (HSP70i$_{Q435A}$), V438K and I440A (HSP70i$_{V438K,I440A}$) or V442A and Y443V (HSP70i$_{V442A, Y443V}$) in the respective peptide sequence exhibit significantly decreased depigmentation effects in the above-described mouse vaccination model (Mosenson et al, 2013). Furthermore, in the early and rapidly depigmenting mouse strain h3TA2, which expresses T-cells bearing a human tyrosinase-reactive TCR transgene and HLA-A2.1, vaccination with a plasmid harboring HSP70i$_{Q435A}$ resulted in a restoration of pigmentation in contrast to mice vaccinated with an empty vector. In mice vaccinated with wild-type HSP70i, a persistent skewing of the DC phenotype towards the inflammatory subset was observed, while conversely in mice vaccinated with HSP70i$_{Q435A}$, a skewing towards the tolerogenic phenotype was observed. Analysis of the humoral immune response to HSP70i revealed that only antibodies that bind downstream of the QPGVLIQVYEGER peptide were generated (Mosenson et al., 2013).

In addition to vitiligo, the role of HSP70i in antigen presentation and DC activation is considered to be involved in the aetiology of many other autoimmune and/or inflammatory diseases, for example skin diseases, such as psoriasis and lupus erythematosus (Wang et al., 2011; Jacquemen et al., 2017), autoimmune diabetes (Millar et al., 2003) and graft-versus-host disease or multiple sclerosis (Mansilla et al., 2012).

Several therapeutic approaches for the treatment of autoimmune diseases, especially of vitiligo, based on HSP70i are suggested in the art.

WO 2009/036349 A1 discloses fusion proteins comprising a trimerizing domain and at least one polypeptide, such as an antibody or fragment thereof that binds to the HSP70i polypeptide QPGVLIQVYEGE. Furthermore, the use of said fusion protein for treating vitiligo is suggested. However, specific antibodies or therapeutic effects obtained by administering antibodies or the disclosed fusion protein are not provided. Based on the dendritic cell activating properties of the C-terminals of HSP70i, the document furthermore suggests the use of a fusion protein comprising a trimerizing domain and the HSP70i polypeptide QPGVLIQVYEGE for use as a vaccine for the treatment of cancer, especially for the treatment of melanoma.

WO 2013/033395 A1 suggests the use of full length HSP70i variants comprising the mutated QPGVLIQVYEG peptide sequence in treating autoimmune diseases. Specifically, the document discloses a DNA vaccine for treating and altering diseases, especially vitiligo, comprising a plasmid encoding full-length HSP70i wherein the HSP70i is an HSP70i$_{Q435A}$ mutant variant. The document discloses that vaccination with DNA constructs expressing wild-type HSP70i accelerated depigmentation. Injection of the plasmid comprising the sequence of mutant HSP70i showed reduced depigmentation in comparison to an empty control vector. However, for these types of DNA vaccines, activation of oncogenes as a result of genomic incorporation of the immunizing DNA is a major safety concern. Furthermore, anti-DNA antibodies might be elicited upon DNA vaccination.

WO 2009/008719 A2 discloses the use of peptides derived from HSP70 members that have been eluted from MHC class II molecules for the treatment of inflammatory or autoimmune diseases. The inflammatory diseases include Crohn's disease, granulomatous colitis, lymphocyte colitis, collagenous colitis, ulcerative colitis and coeliac disease. The autoimmune diseases include arthritis, atherosclerosis, multiple sclerosis and myasthenia gravis, rheumatoid arthritis, psoriatic arthritis and juvenile arthritis. However, vitiligo is not disclosed. The disclosed peptides include peptides from the N-terminal region of HSP70i and peptides derived from amino acids 419 to 436 and 435 to 460 of the C-terminal region. However, no experimental data regarding these peptides are disclosed.

In summary, the treatment options for vitiligo or other autoimmune diseases with an HSP70-related aetiology disclosed in the prior art suffer from limited therapeutic efficacy, significant side effects or safety concerns.

PROBLEM UNDERLYING THE INVENTION

In view of the prior art, it was the general problem underlying the present invention to provide active agents, compositions, methods and uses to overcome the above-mentioned disadvantages of the prior art. Especially, agents, compositions and methods suitable for treating or preventing autoimmune diseases with an HSP70i-related aetiology, especially vitiligo, should be provided. Furthermore, the agents and compositions should be conveniently administrable, safe and easy to manufacture.

DISCLOSURE OF THE INVENTION

Surprisingly, it was found that the problem underlying the invention is solved by the mutated parvovirus protein, compositions, uses and methods according to the claims. Further embodiments of the invention are outlined throughout the description.

In a first aspect, the invention relates to a mutated parvovirus structural protein, comprising at least one insertion comprising a sequence of at least six consecutive amino acids comprised within amino acids 320 to 641 of human HSP70i.

Surprisingly, the inventive parvovirus structural protein induces high titer antibodies against human HSP70i. Furthermore, as evident from FIG. 5, immunization with the mutated parvovirus structural protein inhibits depigmentation based on autoimmune aetiology.

A "mutated" parvovirus structural protein within the present invention is a parvovirus structural protein which comprises at least an insertion comprising a sequence of at least six consecutive amino acids comprised within amino acids 320 to 641 of human HSP70i as consecutive sequence, in comparison the respective wild-type parvovirus structural protein. The mutated parvovirus structural protein may comprise additional mutations, such as substitutions, insertions, and/or deletions as described in the following.

According to the present invention, "HSP70i" refers to the human inducible heat shock protein 70 also known as HSP72, HSP70A1A or HSP70A1B, which are characterized by the same amino acid sequence, but are yet encoded by separate genes with different regulator regions. The amino acid sequence of HSP70i is equivalent to the sequence of Gene Bank accession no. AQY76873.1. The respective amino acid sequence is designated SEQ ID No. 1 in the context of the present invention.

acids 320 to 641 of human HSP70i may also comprise at least 7, at least 8, at least 9, at least 10, at least 11, at least 12, at least 13, at least 14, at least 15, at least 16, at least 17, at least 18, at least 19, at least 10 or at least 21 amino acids. In a further preferred embodiment, the insertion may comprise a sequence of 6 to 40, 10 to 30, or 12 to 25 amino acids, preferably 13 to 18 and most preferably 15 to 17 amino acids. Further to these amino acids, the insert might further comprise N- and C-terminal linker sequences as described below.

In one embodiment at least one insertion may not be full length HSP70i. Preferably, the insertion comprises a sequence of not more than 50, not more than 45, not more than 40, and/or not more than 35 consecutive amino acids comprised within amino acids 320 to 641 of human HSP70i.

Since it is an object of the present invention that the mutated parvovirus structural protein induces the generation of antibodies against HSP70i, the amino acid sequence of the insertion comprises a B-cell epitope. A "B-cell epitope" is the part of a macromolecule that is recognized by the

```
SEQ ID NO 1:
MAKAAAIGID LGTTYSCVGV FQHGKVEIIA NDQGNRTTPS YVAFTDTERL
1                                                   50

IGDAAKNQVA LNPQNTVFDA KRLIGRKFGD PVVQSDMKHW PFQVINDGDK
51                                                 100

PKVQVSYKGD TKAFYPEEIS SMVLTKMKEI AEAYLGYPVT NAVITVPAYF
101                                                150

NDSQRQATKD AGVIAGLNVL RIINEPTAAA IAYGLDRTGK GERNVLIFDL
151                                                200

GGGTFDVSIL TIDDGIFEVK ATAGDTHLGG EDFDNRLVNH FVEEFKRKHK
201                                                250

KDISQNKRAV RRLRTACERA KRTLSSSTQA SLEIDSLFEG IDFYTSITRA
251                                                300

RFEELCSDLF RSTLEPVEKA LRDAKLDKAQ IHDLVLVGGS TRIPKVQKLL
301                                                350

QDFFNGRDLN KSINPDEAVA YGAAVQAAIL MGDKSENVQD LLLLDVAPLS
351                                                400

LGLETAGGVM TALIKRNSTI PTKQTQIFTT YSDNQPGVLI QVYEGERAMT
401                                                450

KDNNLLGRFE LSGIPPAPRG VPQIEVTFDI DANGILNVTA TDKSTGKANK
451                                                500

ITITNDKGRL SKEEIERMVQ EAEKYKAEDE VQRERVSAKN ALESYAFNMK
501                                                550

SAVEDEGLKG KISEADKKKV LDKCQEVISW LDANTLAEKD EFEHKRKELE
551                                                600

QVCNPIISGL YQGAGGPGPG GFGAQGPKGG SGSGPTIEEV D
601
```

The C-terminus of HSP70i is underlined in SEQ ID NO. 1.

According to the present invention, a sequence of at least six consecutive amino acids "comprised within amino acid 320 to 641 of HSP70i" is a sequence of at least six consecutive amino acids that constitute a part of the amino acid sequence within amino acids 320 to 641 of HSP70i.

In a preferred embodiment, the sequence of at least six consecutive amino acids comprised in the insertion are comprised within amino acid 378 to 641 of HSP70i as consecutive sequence.

The at least one insertion comprising a sequence of at least six consecutive amino acids comprised within amino immune system, specifically by antibodies or B-cells. A B-cell epitope can be both a linear amino acid sequence and a structural epitope defined by the surface of the macromolecule which can be built by a secondary structure of amino acids or in combination with other organic substances.

In a preferred embodiment, the amino acid sequence of the insertion may be a sequence of amino acids which correspond to a sequence which is at least partially displayed on the surface of native HSP70i. Preferably, the amino acids are at least partially displayed on the surface of HSP70i in a conformation wherein a substrate polypeptide is bound to HPS70i.

The structure of the C-terminal domain of HSP70i has been solved (Zhang et al., 2014) and can be analyzed with respect to the position of the amino acid sequence of interest.

In a preferred embodiment, the amino acid sequence comprised in the insertion comprises an amino acid sequence which is involved in the activation of antigen-presenting cells, especially dendritic cells, by human HSP70i. The involvement of an amino acid sequence within human HSP70i in the activation of antigen-presenting cells may be tested by analyzing the effect, especially the inhibitory effect, of antibodies that bind to the respective sequence, or by analyzing the effect, especially the inhibitory effect, of one or more mutation introduced into the respective sequence of HSP70i, on the dendritic cell activation by HSP70i. An example for a suitable assay is described in Example 3 of this application. The activation of dendritic cells by HSP70i can, for example, be analyzed by the activation of immature dendritic cells in in vitro cell culture assays as disclosed by Mosenson et al. (2013). In case an antibody which binds to the respective sequence, or a mutation introduced into the respective sequence, inhibits the activation of dendritic cells by HSP70i, the respective sequence is considered to be a "sequence which is involved in the activation of antigen-presenting cells" within the meaning of the present invention.

As disclosed by Mosenson et al. (2013), amino acids 435 to 445 of HSP70i having the amino acid sequence QPGVLIQVYEG (SEQ ID No. 2) are involved in the activation of antigen-presenting cells, for example dendritic cells. Therefore, it is a preferred embodiment of the invention that the insertion in the mutated parvovirus structural protein comprises the sequence of amino acids 435 to 445 of HSP70i with the amino acid sequence QPGVLIQVYEG (SEQ ID No. 2). Most preferably, the insertion in the mutated parvovirus structural protein comprises the sequence of amino acids 430 to 450 of HSP70i, having the sequence TYSDNQPGVLIQVYEGERAMT (SEQ ID No. 3). In a specific embodiment of the invention, the insertion in the mutated parvovirus structural protein does not comprise an amino acid sequence of at least six consecutive amino acids comprised within the amino acids 291 to 304 and/or 445 to 460 of human HSP70i.

In a further embodiment, the amino acid sequence comprised in the insertion comprises at least one mutation in comparison to the corresponding sequence within HSP70i. A "corresponding sequence within HSP70i" is the sequence from which the sequence of the insertion can be derived by introducing mutations. The insertion comprising at least one mutation may have at least 50%, at least 55%, at least 60%, at least 65%, at least 70%, at least 75%, at least 80%, at least 85%, at least 90% or at least 95% amino acid sequence identity to an amino acid sequence within amino acids amino acids 320 to 641 of HSP70i, preferably to amino acids 430 to 450, or amino acids 435 to 445 of HSP70i. The mutated sequence of the insert may induce antibodies against the corresponding sequence within HSP70i when administering a mutated parvovirus protein according to the invention comprising said insert.

In the context of the present invention, a mutation within an amino acid sequence or in a nucleotide sequence may be at least one substitution, insertion or deletion. In a substitution, at least one amino acid or nucleotide is exchanged against another amino acid or a nucleotide in the mutated sequence in comparison to the respective wild type or comparator sequence. In an insertion, at least one amino acid or nucleotide is inserted into the mutated sequence in comparison to the respective wild type or comparator sequence. In a deletion, at least one amino acid or nucleotide is omitted in the mutated sequence in comparison to the respective wild type or comparator sequence.

The substitution may be a conservative amino acid substitutions in the primary sequence. One skilled in the art will understand that the term "conservative substitution" is intended to embrace the act of replacing one or more amino acids of a protein or peptide with an alternative amino acid with similar properties and which does not substantially alter the physical-chemical properties and/or structure of function of the native protein. Analogues of this type are also encompassed within the scope of this invention. In one embodiment, substitute amino acids may be selected from other members of the class to which the amino acid belongs. For example, non-polar (hydrophobic) amino acids include alanine, leucine, isoleucine, valine, glycine, proline, phenylalanine and tryptophan. Polar neutral amino acids include serine, threonine, cysteine, tyrosine, asparagine and glutamine. The positive charged (basic) amino acids include arginine, lysine and histidine. The negative charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free OH is maintained; and Gln for Asn to maintain a free $NH_2$.

In a preferred embodiment, the amino acid sequence comprised in the insertion may comprise amino acids 435 to 445, more preferably amino acids 430 to 450, of HSP70i with at least one mutation in comparison to the corresponding sequence within HSP70i. Preferably, the mutation is at least one amino acid substitution. The at least one mutation may also be two substitutions or three substitutions or more substitutions. Preferably, the at least one mutation in the insertion corresponds to the substitution Q435A (a substitution of Q in position 435 against A), the combined substitution of V438K and I440A, or the combined substitution V442A and Y443V, in the corresponding HSP70i sequence. Most preferably, the mutation is a substitution which corresponds to the substitution of Q435A in HSP70i. Thus, the insertion may preferably comprise the amino acid sequence APGVLIQVYEG (SEQ ID No. 4), more preferably the amino acid sequence TYSDN APGVLIQVYEGERAMT (SEQ ID No. 5). As disclosed above, the aforementioned mutations eliminate the property of HSP70i to activate dendritic cells (Mosenson et al., 2013).

It is a preferred embodiment of the invention that the epitope constituted by the mutated sequence comprised in the insertion of the mutated parvovirus structural, upon administration to a subject, induces the generation of antibodies that bind to the corresponding epitope within HSP70i. The corresponding epitope within HSP70i is at least partially constituted by the amino acid sequence within HSP70i which corresponds to the sequence comprised in the insertion. An epitope which induces antibodies that bind to an epitope constituted by a different amino acid sequence represents a "mimotope". Thus, according to the invention, the mutated amino acid sequence comprised in the insertion represents a mimotope of the corresponding sequence within HSP70i.

The use of an insertion with a mutated sequence in comparison to the corresponding sequence within HSP70i may be an especially advantageous embodiment of the present invention. It is an object of the present invention that the mutated parvovirus structural protein elicits an antibody response against HSP70i in the subject administered with the parvovirus protein. However, antigenic sequences within HSP70i exhibit "self"-antigens to the human immune system. In a process termed central tolerance, B-cells that are reactive to self-antigens undergo a negative selection and are thus deleted to a large extent during the cell maturation. In the embodiment wherein the amino acid sequence of the insertion comprised in the parvovirus structural protein comprises a mutation in comparison to the respective sequence within HSP70i, the epitope of the insertion deviates from the self-antigen. Thus, the probability that B-cells, which are reactive to the insertion and cross-reactive to the self-antigen within human HSP70i, have not been depleted by the mechanism of central tolerance may be increased. Therefore, the use of a mutated amino acid sequence may increase the probability to induce antibodies against HSP70i upon administration of the parvovirus structural protein to a subject to be treated.

Furthermore, the use of a mutated HSP70i sequence as disclosed above, prevents an activation of dendritic cells by the parvovirus protein according to the invention. Thus, the administration of a parvovirus protein comprising an insertion with a mutated HSP70i sequence as disclose above may not promote the autoimmune disease to be treated through the activation of dendritic cells.

The parvovirus structural protein according to the invention may be derived from an adeno-associated virus (AAV), Goose parvovirus, Duck parvovirus, Snake parvovirus, feline panleukopenia virus, canine parvovirus, B19 or minute virus of mice (MVM) and may be mutated as described herein. Within the context of the present invention, the mutated structural protein according to the present invention which is "derived" from another protein has at least 80%, at least 85%, at least 90%, at least 95%, at least 96%, at least 97%, at least 98%, or at least 99% amino acid sequence identity to the respective protein, outside of the sequence of the insert within the mutated structural protein. Due to the high conservation of genome organization amongst the parvoviruses, the invention can easily be transferred to other parvovirus members. Preferably structural protein according to the invention may be derived from a parvovirus that shares the general capsid assembly from viral proteins VP1, VP2 and VP3. Structural proteins derived from these viruses are generally advantageous since they enable a virus-like particle (VLP) production only from VP3 as described below. Presently known viruses of this subgroup include adeno-associated virus (AAV), Goose parvovirus, Duck parvovirus, and Snake parvovirus. Preferably AAV is selected from the group consisting of bovine AAV (b-AAV), canine AAV (CAAV), mouse AAV1, caprine AAV, rat AAV, avian AAV (AAAV), AAV1, AAV2, AAV3b, AAV4, AAV5, AAV6, AAV7, AAV8, AAV9, AAV10, AAV11, AAV12, and AAV13, especially AAV2.

In a preferred embodiment, the mutated parvovirus protein is derived from AAV2. The human immune system in general is well adapted to AAV2 capsid proteins as the largest fraction of the human population is infected with this virus that is not associated with any disease. Further, AAV2 as a gene therapy vector has been tested in large number of human patients and appeared not to be associated to immunological complications or other safety concerns. Accordingly, compared to other backbones aiming to put B-cell epitopes into a multimeric structure, AAV2 has the enormous advantage that the backbone itself, for most of the vaccinated humans, will not generate an unprecedented immune reaction that may cause autoimmune diseases in vaccinated humans.

The mutated parvovirus structural protein according to the present invention may be capable of forming a multimeric structure, wherein the insertion is located on the surface of said multimeric structure. The multimeric structure may for example be a capsomer, a virus-like particle (VLP) or a virus. Epitopes presented by ordered, multivalent, highly repetitive, and often rigid structures of viruses or VLPs can lead to a strong stimulation of B-cells and the induction of robust and long-lasting antibody responses due to extensively crosslink B-cell receptors. The strong signaling may even override B-cell tolerance mechanisms, allowing the induction of potent antibody responses against self-antigens (Frietze et al., 216; WO 2008/145401 A2). Thus, the use of proteins that multimerize into highly repetitive, rigid structures, like parvovirus structural proteins according to the present invention, is especially advantageous for generating antibodies against self-antigens, such as HSP70i.

In a preferred embodiment of the present invention, the parvovirus mutated structural protein is a mutated VP3 protein. It was previously shown (WO 2010/099960 A2) that multimeric structures useful as vaccines can be generated based upon multimeric structures consisting essentially of VP3. The use of multimeric structures comprising only a single structural protein is generally considered advantageous, since clinical development of vaccines based on multimeric structures is simplified for products based on a single active compound/protein and being as pure as possible. With respect to e.g. VLPs this is a problem in general, as viruses are often composed of more than one protein and are capable of packaging specifically viral DNA or unspecifically DNA from the host cell. Accordingly, it is desirable to obtain "pure" VLPs that contain as few different proteins as possible and preferably no nucleic acid. Further, vaccines containing VP1, VP2 and VP3 are generally produced in the presence of the parvoviral Rep protein. Rep does not only represent a further protein that is attached to VLPs but also is held responsible for packaging of virus genomes and unspecific DNA into preformed capsids (King et al., 2001). Packaging of DNA is to be avoided as VLPs potentially can enter cells of a patient and thereby transfect such contaminating DNA, which may cause all sorts of unwanted effects.

Virus-like particles comprising a mutated parvovirus structural protein derived from VP3, which is not N-terminally extended by at least parts of the VP3 sequence, as the only structural protein may be obtained by expressing a mutated parvovirus structural protein derived from VP3 in a cell under control of a Rep-independent promoter. Additionally, a polypeptide designated "assembly activating protein" (AAP) is expressed according to methods as disclosed in Sonntag et al., 2010 or WO 2010/099960 A2, which allows for high yields, e.g. approximately about $10^5$, preferably about $10^6$, and more preferably about $10^7$ virus particles to be formed per cell. The mutated parvovirus structural protein derived from VP3 of a certain virus type may preferably be co-expressed with the corresponding AAP protein from said virus type (Sonntag et al., 2010 or WO 2010/099960 A2). Alternatively an AAP from a closely related virus type may be used. The sequence encoding AAP may be provided either in cis or in trans to assemble capsids consisting essentially of VP3. Virus particle titers can be quantified from lysates of transfected cells (see above) in their undiluted form or in a dilution using a commercially available titration ELISA kit which is based on the binding of the monoclonal antibody A20 to the viral capsid in an assembled state to measure the virus concentration. Since the antibody A20 does not bind to the capsid of e.g. a different virus serotype, particle titers can be visualized by electron microscopy and quantified by counting. To analyze protein expression and estimate its amount cell lysates of identical portions of transfected cells can be processed for SDS-PAGE. Upon gel electrophoresis and transfer to a nitrocellulose membrane, proteins can be probed using binders specific to the target protein (e.g. monoclonal antibodies B1, A69, anti-GFP). The amount of protein translation can be estimated from the amount of binders that specifically bind to the protein. These complexes can be visualized and quantified by e.g. immunohistochemical staining, immunofluorescent staining or radioactive labeling.

In alternative to obtaining the virus-like particles from cell lysates, as disclosed by Sonntag et al., 2010 or WO 2010/099960 A2, the virus-like particles may preferably be obtained from culture supernatant. Obtaining virus-like particles from the culture supernatant advantageously supersedes the cell lysis step in the manufacturing and facilitates the purification of the particles.

It is preferred according to this invention that the insertion(s) is (are) inserted into one or more positions selected from the group consisting of I-261, I-266, I-381, I-447, I-448, I-453, I-459, I-471, I-534, I-570, I-573, I-584, I-587, I-588, I-591, I-657, I-664, I-713 and I-716, preferably I-261, I-453, I-534, I-570, I-573 and I-587, more preferably I-453, I-534 and I-587, especially I-453 and I-587. The used nomenclature I-### refers to the insertion site with ### naming the amino acid number relative to the VP1 protein of AAV-2, however meaning that the insertion may be located directly N- or C-terminal, preferably directly C-terminal of one amino acid in the sequence of 5 Amino acids N- or C-terminal of the given AA, preferably 3, more preferably 2, especially 1 AA(s) N- or C-terminal of the given AA. For parvoviruses other than AAV-2 the corresponding insertion sites can be identified by performing an amino acid alignment or by comparison of the capsid structures, if available. Such alignment has been performed for the parvoviruses AAV-1, AAV-2, AAV-3b, AAV-4, AAV-5, AAV-6, AAV-7, AAV-8, AAV-10, AAV-11, b-AAV, GPV, B19, MVM, FPV and CPV (FIG. 3 of WO 2008/145401 A2).

The amino acid position after which the insertion was introduced and which named the site is underlined. It is also possible likewise to introduce an insertion into the five directly adjacent Amino acids located next to the underlined AA, because these are likewise located within a loop in the AAV2 capsid. For example the insertion site I-587 corresponds to an insertion before and/or after one of the following Amino acids indicated by emphasis: FQSSS__TDPAT in AAV1, LQRGN$_{587}$__RQAAT in AAV2, LQSSN__TAPTT in AAV3b, LQSSS__TDPAT in AAV6, LQAATAAQT in AAV7, LQQQN__TAPQI in AAV8, LQQAN__TGPIV in AAV10, NQNAT__TAPIT in AAV11, and NQSS T__TAPAT in AAV5.

Further, the insertion site I-453 corresponds to an insertion directly N- or C-terminal of the following ten Amino acids each, preferably directly C-terminal of the amino acid indicated by emphasis QNQSG__SAQNK in AAV1, NTPS G$_{453}$__TTTQS in AAV2, GTTSG__TTNQS in AAV3b, QNQSG__SAQNK in AAV6, SNPGG__TAGNR in AAV7, GQTTG__TANTQ in AAV8, QSTGG__TQGTQ in AAV10, LSGET__NQGNA in AAV11 and FVSTN__NTGGV in AAV5.

In a preferred embodiment the parvovirus mutated structural protein of the invention comprises two or more insertions, each comprising at least one amino acid sequence of at least six consecutive amino acids comprised within amino acids 320 to 641 of HSP70i and each inserted at a different insertion site of the parvovirus mutated structural protein, preferably wherein one insertion is at I-587 and one at I-453. The two or more insertions of sequences of at least six consecutive amino acids comprised within amino acids 320 to 641 of HSP70i may be the same sequences or different sequences. Preferably, the sequences are the same sequences, most preferably comprising at least the sequence APGVLIQVYEG.

In addition to the insertion of an amino acid sequence of at least six consecutive amino acids comprised within amino acids 320 to 641 of HSP70i, or mutants thereof, having a length as described above, the insertion may additionally preferably comprise on its N- and/or C terminus a linker sequence which preferably has a length of 2 to 10, more preferably 3 to 6 amino acids, Preferably the linker comprises or consists of small neutral or polar amino acids (A, G, S, C), which support the inserted epitope to be well accessible to the immune system. C has the advantage that two C on both sides of the linker may be able to form a hydrogen bond. Therefore, it is envisaged that both the N-terminal and C-terminal linker contain at least one C. Generally, it is preferred that the linker sequence(s) is (are) composed of A, G and S.

In a further preferred embodiment of the invention none of the 5 amino acids directly adjacent to the insertion is R and none of the amino acids of the linker, if present, is R. R in close proximity to the insertion reduces yield of the mutated structural protein/the multimeric structures composed of the mutated structural protein during expression and purification, and therefore is preferably avoided. Accordingly, the Rs at position 585 and 588 for AAV2 have been substituted for example by A. Accordingly, the parvovirus mutated structural protein comprises one or more additional mutations selected from an insertion, a deletion, a N- or C-terminal fusion of a heterologous amino acid sequence and a substitution, particularly a single-amino-acid exchange, or a combination of these, preferably a mutation of R585 of AAV2 and/or R588 of AAV2, especially a single-amino-acid exchange R585A of AAV2 and/or R588A of AAV2.

Additionally, the insertion of epitopes at position I-453 of AAV2 as described in WO 2008/145401 A2 leads to the generation of an R within the linker downstream of the insertion (see example 6.4.3, page 103, lines 12 and 14) due to the generation of a useful endonuclease restriction site. Parvovirus mutated structural proteins where this R was substituted for a small neutral or polar amino acid (in the examples for S in a R453S mutant) lead to considerably higher yield of VP3 only AAV virus-like particles (AAVLPs) during expression and subsequent purification. Therefore, it is preferred, that the linkers, if present, do not contain an R, especially that the linker directly downstream of the inserted epitope at I-453 does not contain an R.

In a further aspect, the invention relates to a multimeric structure comprising parvovirus mutated structural proteins as described above, particularly comprising at least 5, preferably at least 10, more preferably at least 30, most preferably at least 60 structural proteins. Such multimeric structure may be a capsomer, a virus-like particle (VLP) or a virus. Capsomers are multimeric subunits of a viral capsid, typically consisting of 5-6 capsid proteins (pentamers and hexamers). VLPs are empty viruses, meaning that they do not comprise genetic material such as a viral genome or relevant part thereof. Alternative to ordered structures like capsomers, a virus-like particles (VLPs) or a viruses, the multimeric structures may be aggregates with amorphous structures with no symmetric order. Preferably the insertion comprising a sequence of at least six consecutive amino acids comprised within amino acids 320 to 641 of HSP70i, or mutants thereof, is located on the surface of the multimeric structure.

Another embodiment of the present invention relates to a nucleic acid coding for a parvovirus mutated structural protein of the invention such as DNA, RNA, mRNA etc. A further embodiment of the present invention is a vector, e.g. a virus that comprises a nucleic acid encoding the parvovirus mutated structural protein of the invention. Such virus may be infectious or inactive, for example it may have been inactivated through standard techniques such as attenuation or irradiation.

In a further embodiment, the present invention is a cell comprising a nucleic acid coding for the parvovirus mutated structural protein as described above. Such cell can be a bacterium, preferably *E. Coli*, a yeast cell, preferably *S. Cerevisiae, Hansenula Polymorpha* or *Pichia Pastoris, k. lactis*, an insect cell, preferably SF-9, SF+ or High5, or a mammalian cell, preferably HeLa, 293, VERO, PERC6, BHK or CHO.

The parvovirus mutated structural proteins of the invention can be prepared by a method comprising the steps of:
a) producing the structural protein by cultivating the cell according to the invention under suitable conditions thereby expressing the nucleic acid of the invention, and optionally co-expressing a nucleic acid encoding an assembly activating protein (AAP), and
b) optionally isolating the expressed parvovirus mutated structural protein produced in step a).

In a preferred embodiment, essentially only VP3 is expressed, leading to multimeric structures comprising essentially only VP3. Expression and purification according to this method may for example be performed in accordance with Example 1 of this application. Expression of parvovirus mutated structural proteins comprising an insertion and purification of the obtained AAVLPs is furthermore disclosed in WO 2012/031760 A1, Example 1, for mammalian cells or by WO 2010/099960 A2, Example 1, for insect cells.

Another subject of the invention relates to a composition comprising at least one parvovirus mutated structural protein according to the invention and/or a nucleic acid according to the invention, and/or preferably at least one multimeric structure according to the invention.

In a further aspect, the invention relates to a parvovirus mutated structural protein according to the invention and/or a nucleic acid according to the invention, preferably a multimeric structure according to the invention, for use as a medicament. Furthermore, the invention relates to a composition comprising at least one parvovirus mutated structural protein according to the invention and/or a nucleic acid according to the invention, preferably at least one multimeric structure according to the invention, for use as a medicament.

The medicament may preferably be used as a vaccine comprising at least one parvovirus mutated structural protein of the invention and/or a nucleic acid of the invention, preferably at least one multimeric structure of the invention.

The medicament and/or vaccine may preferably be for use in a method for treating or preventing an autoimmune and/or inflammatory disease or in a method of immunosuppression. The autoimmune and/or inflammatory disease may be selected from vitiligo, aleopecia, arthritis, especially rheumatoid arthritis, psoriasis, lupus erythematosus, multiple sclerosis, Parkinson's disease, autoimmune diabetes (type 1 diabetes), graft versus host, host versus graft reaction Neuromyelitis optica (NMO), Acute optic neuritis (AON), coophorytis, and tumors expressing HSP70. The method of immunosuppression may preferably be a method wherein an immunoreaction in a subject against transplanted tissue, especially against a transplanted organ, is suppressed. Within the context of the present invention, "treating or preventing" a disease or condition, relates to the application of a compound or composition as described herein, to (a) preventing the disease or condition or symptom thereof from occurring in a subject which may be predisposed to and/or may acquire the disease or condition or symptom thereof, but has not yet been diagnosed as having it; (b) inhibiting the disease or condition symptoms, i.e. arresting its development; or (c) relieving or eliminating the disease or condition symptoms, i.e. causing regression of the disease or condition or symptoms thereof. For vitiligo, the symptoms are the depigmentation of skin as described above.

In a further embodiment, the invention relates to the use of the parvovirus mutated structural protein according to the invention and/or a nucleic acid according to the invention, and/or a composition comprising said protein or nucleic acid in the treatment or prevention of an autoimmune and/or inflammatory disease as described herein. The composition may be any medicament disclosed herein.

In a preferred embodiment, the composition, medicament or vaccine encompasses pharmaceutically acceptable carriers and/or excipients. The pharmaceutically acceptable carriers and/or excipients useful in this invention are conventional and may include buffers, stabilizers, diluents, preservatives, and solubilizers. Remington's Pharmaceutical Sciences, by E. W. Martin, Mack Publishing Co., Easton, Pa., 15th Edition (1975), describes compositions and formulations suitable for pharmaceutical delivery of the (poly) peptides herein disclosed. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, citric acid or the like as a vehicle. For solid compositions (e. g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition, medicament or vaccine may further comprise an immunostimulatory substance such as an adjuvant. The adjuvant can be selected based on the method of administration and may include mineral or plant oil-based adjuvants, Montanide incomplete Seppic adjuvant such as ISA, oil in water emulsion adjuvants such as the Ribi adjuvant system, syntax adjuvant formulation containing muramyl dipeptide, or aluminum salt adjuvants. Preferably, the adjuvant is an oil-based adjuvant, preferably ISA206 (SEPPIC, Paris, France), most preferably ISA51 or ISA720 (SEPPIC, Paris, France). In another preferred embodiment the parvovirus mutated structural protein is co-formulated with at least one suitable adjuvant such as CpG, Imidazoquinolines, MPL, MDP, MALP, flagellin, LPS, LTA, or cholera toxin or derivative thereof, saponins, QS21, ISCOMs, CFA, SAF, MF59, adamantanes, aluminum hydroxide, aluminum phosphate or a cytokine.

In a more preferred embodiment, the immunostimulatory substance is selected from the group comprising polycationic polymers, especially polycationic peptides such as polyarginine, immunostimulatory deoxynucleotides (ODNs), peptides containing at least two LysLeuLys motifs, especially KLKLLLLLKLK, neuroactive compounds, especially human growth hormone, alumn, adjuvants or combinations thereof. Preferably, the combination is either a polycationic polymer and immunostimulatory deoxynucleotides or of a peptide containing at least two LysLeuLys motifs and immunostimulatory deoxynucleotides. In a still more preferred embodiment the polycationic polymer is a polycationic peptide. In an even more preferred embodiment of the invention the immunostimulatory substance is at least one immunostimulatory nucleic acid. Immunostimulatory nucleic acids are e.g. neutral or artificial CpG containing nucleic acids, short stretches of nucleic acids derived from non-vertebrates or in form of short oligonucleotides (ODNs) containing non-methylated cytosine-guanine dinucleotides (CpG) in a defined base context (e.g. as described in WO 96/02555). Alternatively, also nucleic acids based on inosine and cytidine as e.g. described in WO 01/93903, or deoxynucleic acids containing deoxy-inosine and/or deoxyuridine residues (described in WO 01/93905 and WO 02/095027) may preferably be used as immunostimulatory nucleic acids in the present invention. Preferably, mixtures of different immunostimulatory nucleic acids are used in the present invention. Additionally, the aforementioned polycationic compounds may be combined with any of the immunostimulatory nucleic acids as aforementioned. Preferably, such combinations are according to the ones described in WO 01/93905, WO 02/32451, WO 01/54720, WO 01/93903, WO 02/13857 and WO 02/095027 and the AU application A 1924/2001.

In a preferred embodiment, the composition, medicament or vaccine may not comprise a further immunostimulatory substance such as an adjuvant as described above. Advantageously, the AAV backbone itself has a strong immune stimulatory property.

The composition, medicament or vaccine according to the invention may be administered to a subject in need thereof, preferably a mammal, most preferably a human, in any conventional manner, including different routes, e.g. by intravenous, intraperitoneal, intra-lymph node, subcutaneous, intradermal, intramuscular, topical, intranasal or intrabronchial administration. Preferably, the composition, medicament or vaccine is administered subcutaneous or intramuscular.

The volume of each dose for administration is preferably up to about 5 ml, still more preferably between 1 ml and 3 ml, and most preferably about 2 ml. The volume of the dose when intramuscular injection is the selected administration route is preferably up to about 5 ml, preferably up to 3 ml, preferably between 1 ml and 3 ml, more preferably between 0.5 ml and 2 ml, and most preferably about 1 ml. The amount of vaccine in each dose should be enough to confer effective immunity against HSP70i protein and decrease the risk of developing clinical signs associated with the autoimmune disease the patient is suffering from or has a chance of developing, or prevents or reverts organ transplant rejection to a subject receiving a vaccination therewith.

Preferably, the unit dose of protein or nucleic acid should be up to about 5 µg protein/kg body weight, more preferably between about 0.2 to 3 µg/kg, still more preferably between about 0.3 to 1.5 µg/kg, more preferably between about 0.4 to 0.8 µg/kg, and still more preferably about 0.6 µg/kg. Alternative preferred unit doses could be up to about 6 µg protein or nucleic acid/kg body weight, more preferably between about 0.05 to 5 µg/kg, still more preferably between about 0.1 to 4 µg/kg.

The dose is preferably administered 1 to 4 times, especially 1 to 3 times, e.g. with an interval of 1 to 3 months. Preferred amounts of protein per dose are from approximately 1 µg to approximately 1 mg, more preferably from approximately 5 µg to approximately 500 µg, still more preferably from approximately 10 µg to approximately 250 µg and most preferably from approximately 25 µg to approximately 100 µg.

In still a further embodiment the invention relates to a method for vaccination and/or for treating or preventing the diseases specified herein by administering to a patient, preferably a mammal, most preferably a human, an effective amount of a parvovirus mutated structural protein, nucleic acid, composition, medicament or vaccine according the invention. Accordingly, the parvovirus mutated structural protein, composition or vaccine according to the invention can be used in a method of preventing or treating an autoimmune and/or inflammatory disease. The autoimmune and/or inflammatory disease may be selected from vitiligo, aleopecia, arthritis, especially rheumatoid arthritis, psoriasis, lupus erythematosus, multiple sclerosis, Parkinson's disease, autoimmune diabetes (type 1 diabetes), graft versus host, host versus graft reaction Neuromyelitis optica (NMO), Acute optic neuritis (AON), oophorytis, and tumors expressing HSP70.

An "effective amount" of a parvovirus mutated structural protein, nucleic acid, composition, medicament or vaccine may be calculated as that amount capable of exhibiting an in vivo effect, e.g. preventing or ameliorating a sign or symptoms. Such amounts may be determined by one of skill in the art.

Above mentioned problems are solved by the invention as claimed and disclosed herein.

Surprisingly, the inventive parvovirus structural protein induces high titer antibodies against human HSP70i, especially against a sequence within HSP70i which is involved in the activation of dendritic cells. The induced antibodies inhibit autoimmune depigmentation.

As shown in Example 2 herein, AAV virus like particles according the present invention, comprising mutated residues 430 to 445 (TYSDNAPGVLIQVYEG) (SEQ ID No. 5) of HSP70i (AAVLP-HSP70i-453$_{Q435A}$) induce significant antibody titers upon vaccination of a mammal. Notably, as shown in FIG. 1, the antibodies comprised in the sera of the immunized animals recognized peptides comprising the HSP70i wildtype residues 430 to 445 (TYSDN QPGVLIQVYEG) (SEQ ID No. 3), peptides comprising respective mutated residues 430 to 445 (TYSDN APGVLIQVYEG) (SEQ ID No. 5) and also the full length natively folded human recombinant HSP70i protein.

As shown in Example 3, the in vivo generated antibodies according to the present invention facilitate a significant inhibition of DC activation tested in vitro. Notably, the inhibition obtained was in the same range as the inhibition by a monoclonal anti-HSP70i antibody. Thus, it can be concluded that vaccinations with AAVLP-HSP70i according to the invention are able to induce antibodies in the respective subject which are suitable for HSP70i inhibition in this subject.

Since the activation of dendritic cells by HSP70i is involved in the aetiology of autoimmune diseases, especially in the aetiology of vitiligo, the parvovirus structural protein is suitable for the treatment and/or prevention of autoimmune diseases, especially vitiligo. Accordingly, it could be shown by the experiments in Example 4 of the present application, that immunization with virus like particles according the present invention inhibited depigmentation in a vitiligo in vivo mouse model.

The use of VLPs comprising the parvovirus structural protein is especially advantageous since these VLPs induce high antibody titers. In contrast to the administration of corticosteroids that is associated with significant side effects, the administration of VLPs is usually not associated with side effects. Furthermore, in contrast to the present treatments of vitiligo, which have to be frequently administered over a prolonged period of time, vaccination with VLPs comprising the respective parvovirus structural protein usually only requires very few administrations, as confirmed by Example 4.

In contrast to prior art therapies, which for example employ vaccination with plasmids encoding full length Hsp70i, the present invention establishes a therapeutic effect by displaying only a short sequence of the self antigen Hsp70i, thus avoiding generation of self antibodies against the entire rest of the protein which is overexpressed in the prior art plasmid vaccination therapies disclosed by WO 2013/033395 A1.

The present invention shall be explained in more detail by the following figures and examples.

FIGURES

EXAMPLES

Figure 1:
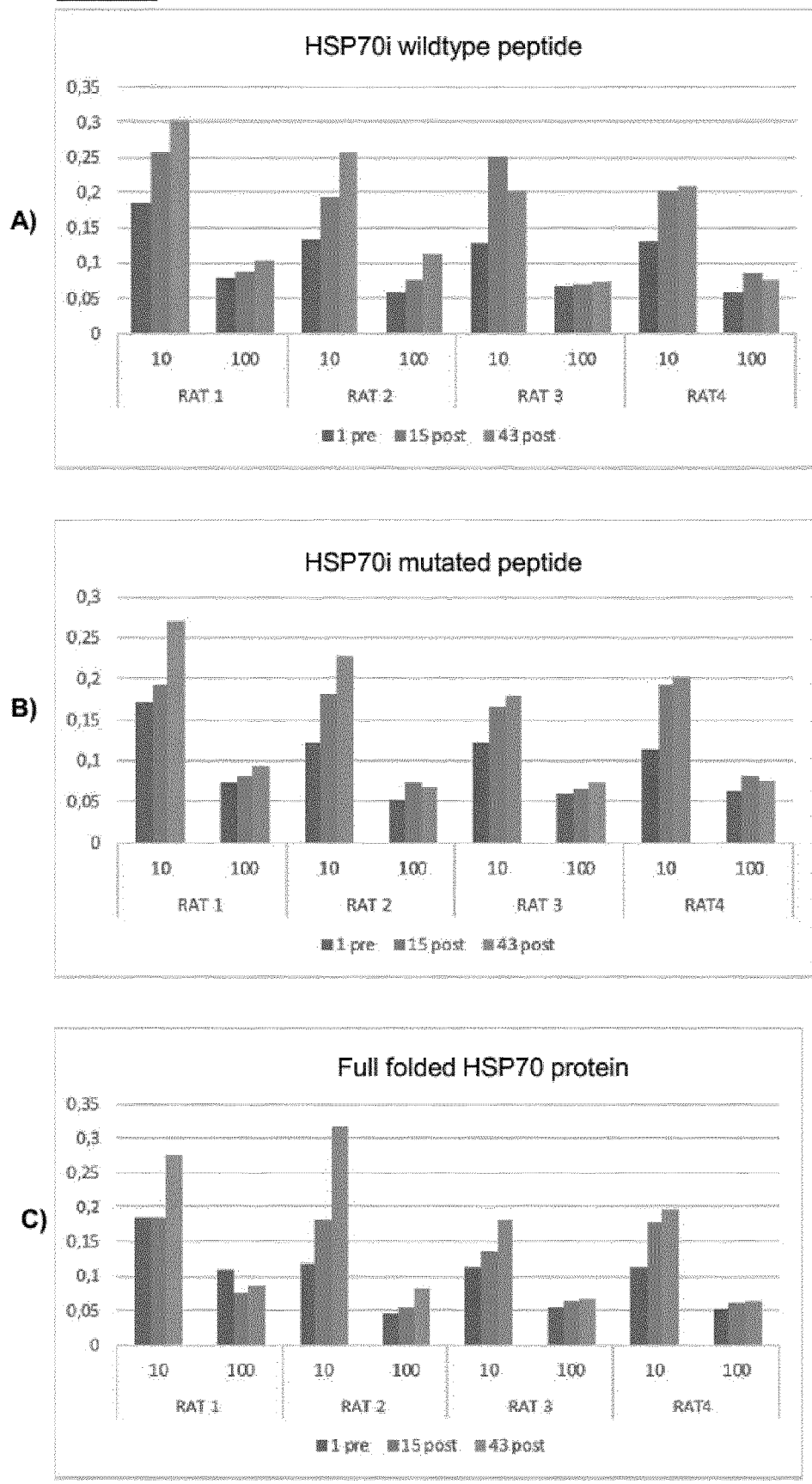
FIG. 1 shows the result of an ELISA assay of antibody titer from pre-immune sera obtained 15 and 43 days after immunization with HSP70i wildtype peptide (FIG. 1A), with HSP70i mutated peptide (FIG. 1B) and full folded HSP70 protein (FIG. 1C) as OD-values at different dilutions.
Figure 2:
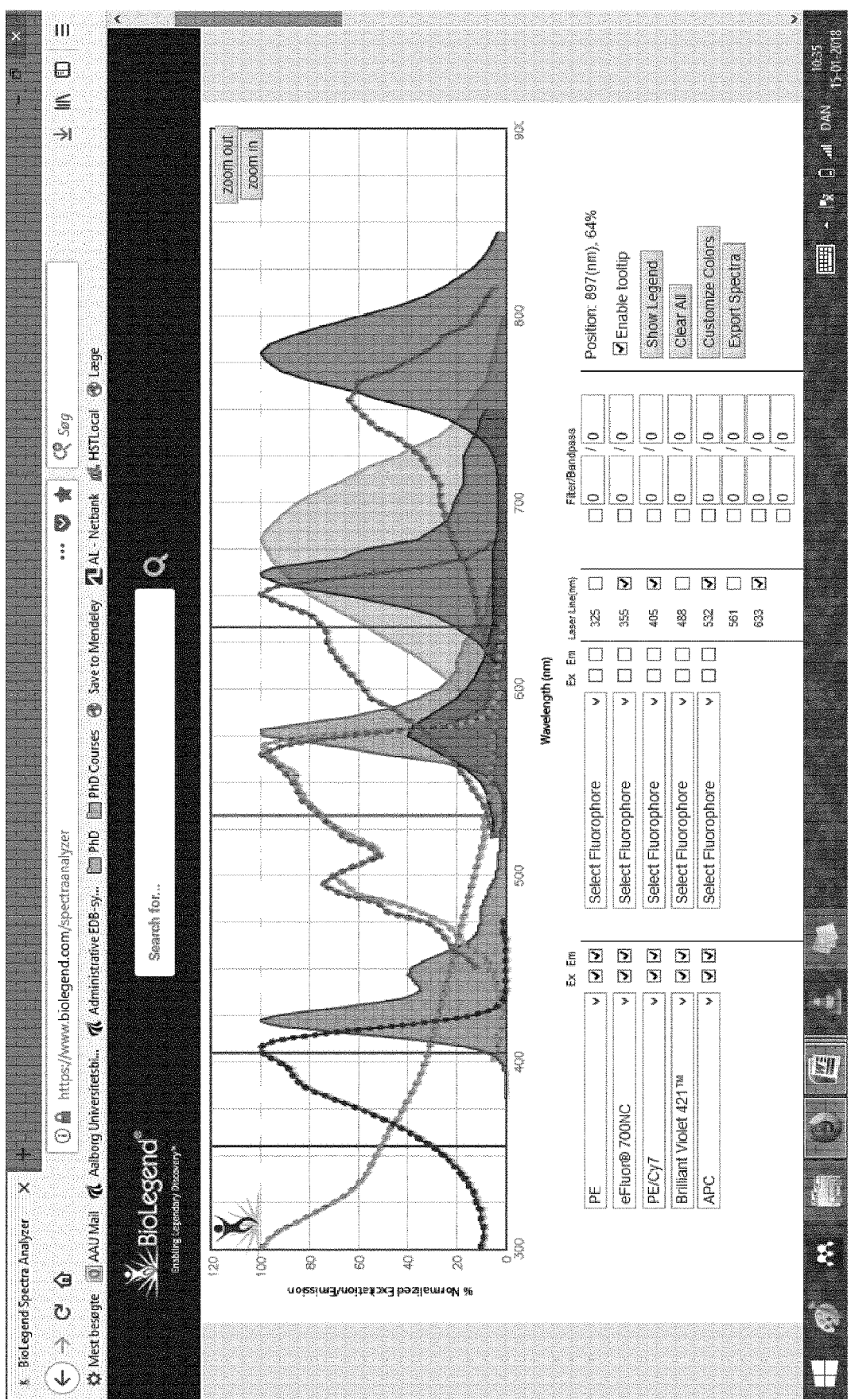
FIG. 2 shows a screenshot of the flow cytometer settings as used in Example 3.

Example 1: Generation of AAVLP-HSP70i VLPs 1.1 Cell Lines and Culture Conditions Human embryonic kidney (HEK) 293T cells were cultivated in T175 flasks and maintained in Dulbecco Modified Eagle Medium (DMEM) supplemented with 10% heat-inactivated fetal-calf serum, 100 U of penicillin/mL, and 100 µg of streptomycin/mL at 37° C. in 5% $CO_2$.

1.2. Cloning of AAVLP-HSP70i

AAVLPs were generated from a plasmid containing overlapping AAV2 VP2 and VP3 coding sequences cloned into the XhoII and NotI site of the pCI plasmid (Promega, Madison, Wis.). The start codon of VP2 was destroyed by introducing a point-mutation using the Quick Change Site-Directed Mutagenesis kit (Agilent Technologies, La Jolla, Calif.) to generate the plasmid pCIVP2mutACG. The point-mutation resulted in an ACG to GAG mutation. In order to introduce peptides into the VP3, the plasmid pCIV2mutACG was modified. The plasmid pCIVP2mutACG-I587 was generated by introduction of NotI and BspEI sites at position 587. The plasmid pCIVP2mutACG-I453 was generated by introduction of NotI and BspEI sites at position 453. Afterwards, yet another point-mutation was introduced using the Quick Change Site-Directed Mutagenesis kit to destroy an additional NotI site within the backbone of the pCI vector generating the plasmid pCIVP2mutACG_mutNotI-I587 and the plasmid pCIVP2mutACG_mutNotI-I453.

The nucleotide sequence of wildtype residues 430 to 445 (TYSDNQPGVLIQVYEG) of HSP70i and mutated residues 430 to 445 (TYSDNAPGVLIQVYEG) of HSP70i was cloned into either the NotI/BspEI digested pCIVP2mut ACG_mutNotI-I587 or the NotI/BspEI digested pCIVP2mutACG_mutNotI-I453 to generate four different plasmids for the AAVLP-HSP70i production. Plasmids and derived proteins AAVLP-HSP70i_Q435A_453 comprised mutated residues 430 to 445 in the 453 insertion site, whereas AAVLP-HSP70i_Q435A_587 comprised mutated residues 430 to 445 in the 587 insertion site.

1.3 Production and Purification of AAVLP-HSP70i

HEK293T cells were transfected with AAVLP-HSP70i plasmid DNA (36 µg per T175 flask mixed with PEI I (1:4)) in serum free DMEM+1% P/S. Supernatant was collected after 3-4 days and the medium was cleared by filtration, diluted three times in dilution buffer (15 mM Sodium Citrate, 6 mM EDTA, 0.001% F-68, pH 5.5±0.3) and adjusted to pH 6.0. Particles were further purified through chromatography. Briefly, the cleared supernatant containing the AAVLPs were loaded onto a Capto S column (GE Healthcare) and after washing with buffer A containing (10 mM Sodium Citrate, 50 mM NaCl, 2 mM EDTA, 0.001% F-68, pH 6.0±0.3) a gradient elution from 0-30% was applied with buffer B (50 mM TrisHCl, 1M NaCl, 2 mM EDTA, 0.001% F-68, pH 8.5±0.3) and fractions were collected during this gradient.

Purity was determined by Western Blotting. The titer was determined using the AAV2 Titration ELISA.

1.4 SDS-PAGE and Western Blotting

Figure 4:
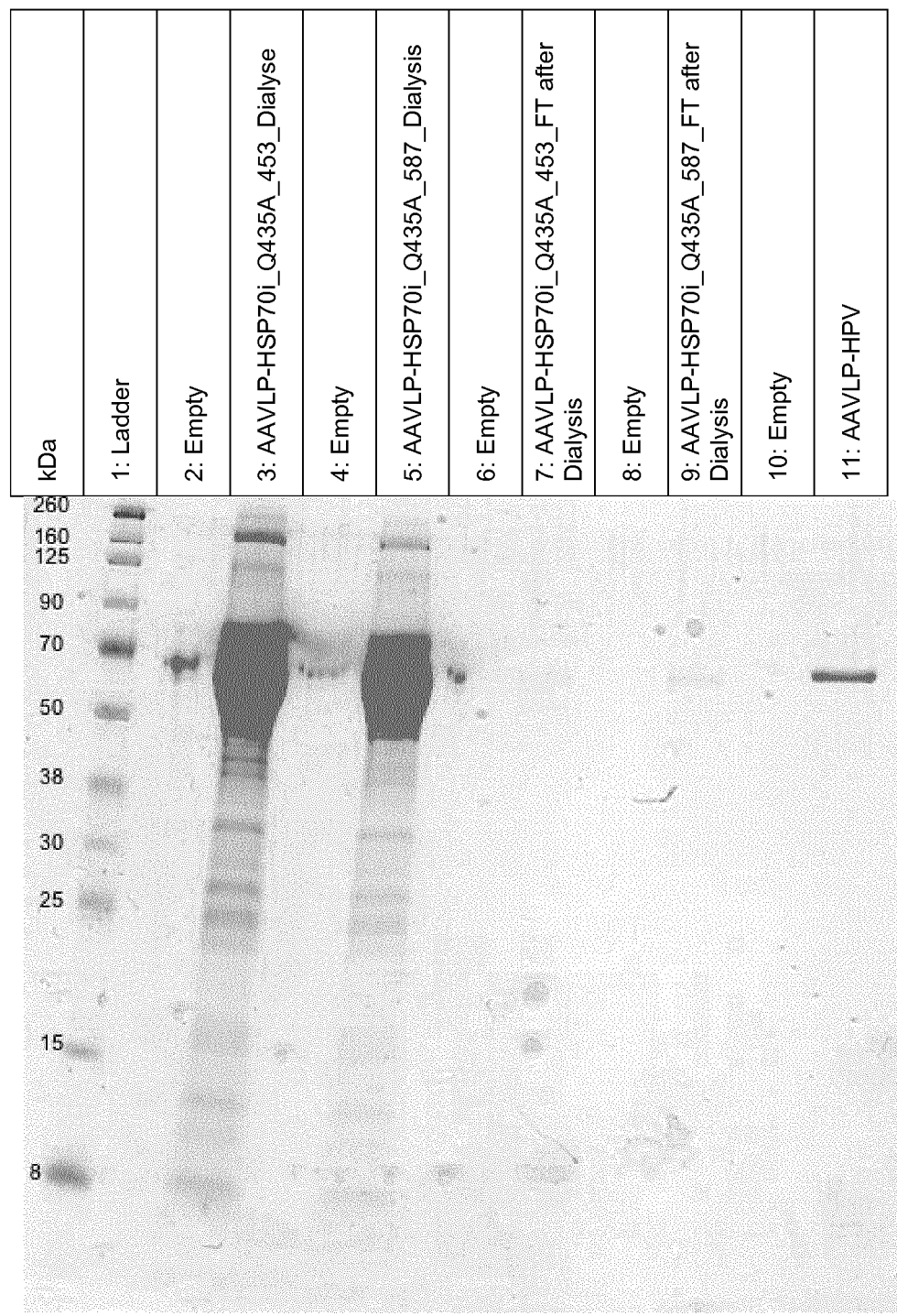
FIG. 4 shows a coomassie blue stained SDS PAGE gel of purified and dialysed HSP70i_Q435A_453 and AAVLP-HSP70i_Q435A_587 particles and the flow through of the respective dialysis.

Fractions of purified AAVLP-HSP70i particles were analysed and identified by SDS-PAGE and coomassie blue staining in order to identify the molecular weight of the purified AAVLP-HSP70i_Q435A vaccine particles. Prior to SDS PAGE samples were dialyzed (samples AAVLP-HSP70i_Q435A_453_Dialyse and AAVLP-HSP70i_Q435A_587_Dialyse). In addition to the dialysed samples, samples from the flow through of the dialysis were analysed (samples AAVLP-HSP70i_Q435A_453_FT and AAVLP-HSP70i_Q435A_587_FT). Chameleon Duo Prestained protein ladder (Licor, #928-60000) was used as size indicator. AAVLPs comprising an HPV epitope insert as disclosed in WO2012031760 (A1) were used as comparison. Results are shown in FIG. 4. Loading of the gel lanes was perfumed as follows: 1: DNA Size Ladder; 2: Empty; 3: AAVLP-HSP70i_Q435A_453_Dialyse; 4: Empty; 5: AAVLP-HSP70i_Q435A_587_Dialysis; 6: Empty; 7:

AAVLP-HSP70i_Q435A_453_FT after Dialysis; 8: EmptyAAVLP-HSP70i_Q435A_587_FT after Dialysis; 9: Empty; 10: AAVLP-HPV The HSP70i_Q435A VP3 proteins HSP70i_Q435A_453 and AAVLP-HSP70i_Q435A show a molecular weight around 65 kDa in agreement with a comparable control VP3 protein.

Expression and purity of the AAVLP-HSP70i VP3 proteins was verified by Western blotting using an antibody. The blotted membrane will be incubated with 5% skim milk in 1×PBS/0.1% Tween-20 for 1 hour at RT followed by incubation of the membrane with antibody (to be decided) for 1 hour at RT. After washing, bound antibodies will be detected with 1:20,000 diluted HRP-labelled anti-X IgG analysed by Odyssey® FC imaging system (LiCor, Lincoln, USA).

1.6 Capsid Titer Determination by AAV2 Titration ELISA

Capsid titer in HEK293T cells as described under 1.3 may be determined using a commercially available AAV2 titration ELISA kit (Progen, #PRATV) according to the manufacture's manual. Briefly, the particles are serial diluted and incubated in a 96-well plate coated with mouse monoclonal antibody to AAV2 for 1 hour at 37° C. After washing, the captured AAVLP-HSP70i particles are incubated with an anti-AAV2 biotin-conjugated monoclonal antibody for 1 hour at 37° C. The washing is repeated and a streptavidin peroxidase conjugate is added to react with the biotin molecule followed by incubation for 1 hour at 37° C. After washing, a substrate solution is added resulting in a colour reaction, which is proportional to the amount of specifically bound viral particles. A stop solution is added after 15 minutes of incubation at RT. The absorbance (OD) is measured photometrically using an ELISA reader at 450 nm. A kit control containing AAV2 particles is included and serial diluted in two-fold resulting in a typical titration curve. The curve allows quantitative determination of the AAVLP-HPS70i capsid titer.

The following titers were determined:
AAVLP-HSP70i_587_Q435A: 1.67E+12 particles/mL (1.187 mg/mL)
AAVLP-HSP70i_453_Q435A: 1.23E+12 particles/mL (1.532 mg/mL)

Example 2: Immunisation of Rats

2.1 Immunisation

In order to analyse the specific immune response against the mutated epitope of HSP70i introduced by the AAVLP-HSP70i-587$_{Q435A}$ or the AAVLP-HSP70i-453$_{Q435A}$ four SPF Wistar rats (strain Crl:WI(Han)) were vaccinated subcutaneously twice (day 1 and day 29) with 8 µg/mL protein (8.7 to 10.0E9 particles/mL) of AAVLP-HSP70i particles obtained according to Example 1. Serum samples were obtained before treatment and 14 days after each vaccination by sublingual method for the first two and by periobital method for the last serum sample collection.

2.2 Determination of Antibody Titers

2.2.1 Materials 8 rat sera samples
Primary anti-HSP70/72, mAb mouse IgG1 (Enzo, #C9F3A-5, Lot.: 05021648,1 mg/mL)
Peptides: JPT, HSP70iwt (pep-1) and HSP70i$_{Q435A}$(pep-2)
Recombinant HSP70 humane (Sigma-Aldrich, #H7283-50UG, stock 300.3 µg/mL)
96-well plates F-bottom (Thermo Scientific Nunc)
Phosphate Buffered Saline (10X).067M (PO$_4$) (HyClone, #SH30258.01, Lot: AAD202603)
Sterile 1×PBS
TWEEN® 20 BioXtra, viscous liquid (Sigma-Aldrich, #9005-64-5, P7949-500 mL, Lot: SLBQ0097V)
Skim Milk Powder (Merck Millipore, #999999-99-4, catalog number: 1.15363.0500)
BSA (BSA, HS, Standard Grade, Europa Bioproducts #EQBAH62-1000, Lot: 62-1381)
Rabbit anti-rat IgG (H+L), HRP-conjugated, ThermoFischer, Invitrogen, #61-9520 (1:1000)
Polyclonal goat anti-mouse Immunoglobulins, HRP-conjugated, Dako #P0447 (1:5000)
Ultra TMB-ELISA Substrate Solution (Thermo Fisher Scientific #12617087, catalog number: 34029)
1.0 M H$_2$SO$_4$ (Bie & Berntsen, #222942)
ELISA reader

2.2.2 Experimental Procedures

Anti-mutated HSP70i-specific IgG-antibodies were measured by ELISA. Briefly, F96 microplates (Nunc, Thermo Scientific) were coated overnight at 4° C. with 1 µg/well of either the biotinylated HSP70i wildtype or the HSP70i mutated peptide. To demonstrate recognition of the full folded HSP70 protein, plates coated with 1 µg/well human recombinant HSP70 (Sigma-Aldrich, #H7283) was also included. Plates were blocked with 5% skim milk in 1×PBS/0.1% Tween-20 for 1 hour at RT followed by incubation with either 1:10 or 1:100 diluted rat sera for 1 hour at 37° C. After washing with 1×PBS/0.1% Tween-20 bound AAVLP-HSP70i antibodies were incubation with 1:1000 diluted HRP-labels anti-rat IgG (H+L) (Thermo Fischer, Invitrogen, #61-9520). The enzymatic reaction was detected by adding TMB-substrate solution (Thermo Fisher Scientific #12617087) resulting in a color reaction, which intensity measured in OD value was analysed using an ELISA reader at 450 nm.

2.3 Results

The antibody titer in pre-immune sera obtained 15 and 43 day after immunization is graphically depicted as OD-values at the different dilutions in FIG. 1A for HSP70i wildtype peptide, FIG. 1B for HSP70i mutated peptide and FIG. 1C for the full folded HSP70 protein.

As evident from the figures, antibodies were efficiently induced in all animals. The antibodies recognize the wildtype peptide, the mutant peptide and the native, fully folded HSP70i. Thus, the data full confirm the approach of generating antibodies against HSP70i by immunization with the AAVLPs according to the invention.

Example 3: DC Activation Assay

The effect of antibodies generated against AAVLP-HSP70i on the activation of dendritic cells was tested in an in-vitro DC activation assay to proof the cellular mechanism underlying the invention.

The assay was performed as follows:

3.1 Isolating PBMCs from Peripheral Blood

3.1.1 Introduction

PBMCs are cells from peripheral blood containing one round nucleus. These cells include all kinds of lymphocytes (T cells, B cells and NK cells), monocytes and dendritic cells. The distribution of these cells in the PBMC population is typically: T cells, 45-70%, B cells and NK cells, up to 15%, monocytes 10-30% and dendritic cells 1-2%. PBMCs can be isolated from human blood, either from full blood or from buffycoats, using density gradient centrifugation.

3.1.2 Definitions

PBMCs—Peripheral Blood Mononuclear Cells
PBS—Phosphate buffered saline

3.1.3 Materials

TABLE 1

| Chemicals/Liquids | Manufacture and Cat. No. | Stock Concentration/Volume |
|---|---|---|
| RPMI1640 medium | Invitrogen, #42401018 | 500 ml |
| Lymphoprep | Medinor, #1114545 | Density, 1.077 ± 0.001 g/ml |
| PBS | Amresco, #E504-500 ml | 500 ml |
| Methyl violet | Ampliqon A/S, #AMPQ00315 | >0.001% methyl violet 2B >0.1% acetic acid |

TABLE 2

| Equipment | Manufacture and Cat. No. | Size |
|---|---|---|
| Sodium Heparin Tubes | Starstedt, #01.1613.100 | 7.5 ml |
| Centrifuge Tube | VWR, #89039-664, #89039-656 | 15 ml, 50 ml |
| Hemocytometer | — | — |

Buffers were prepared one day prior to PBMC isolation:
A) 50 ml of culture medium (RPMI1640+10% FBS+1% P/S) was prepared by:
  Transfer of 45 mL RPMI medium to a 50 mL plastic tube
  Add of 5 mL sterile FBS
  Add of 500 µl P/S
B) 50 ml of Miltenyi buffer (PBS+0.5% BSA+2 mM EDTA) was prepared by:
  Transfer of 50 mL sterile PBS to a 50 mL tube
  Add of 0.25 g BSA
  Add of 500 µl EDTA (from stock 200 mM)
  Sterile filtering the solution using 0.22 µm filer

3.1.4 Experimental Procedures

For one assay, approximately $90 \times 10^6$ PBMCs were isolated from 12 tubes of blood.
The preparation was performed according to the following steps in the respective order:
  Centrifuge tubes containing lymphoprep were prepared by:
  15 ml tubes: add 4 ml lymphoprep
  50 ml tubes: add 15 ml lymphoprep
  Blood from human donor was tabbed in 7.5 ml sodium heparin tubes/get buffycoats
  Full blood was diluted 1:2 in RPMI1640
  Diluted blood was carefully added to the centrifuge tubes containing lymphoprep by letting it run down the side of the tube superimposing on top of the lymphoprep.
  For 15 ml tubes 8 ml diluted blood was added
  For 50 ml tubes 30 ml diluted blood das added
  Cells were centrifuged for 20 min at 180 g, 20° C., acceleration: 2, break: 0.
  The top layer of the supernatant was removed
  For 15 ml tubes 2 ml supernatant were removed
  For 50 ml tubes 7.5 ml supernatant were removed
  The cells for 20 min at 380 g were centrifuged, 20° C., acceleration: 2, break: 0.
  15 ml centrifuge tubes with 8 ml cold PBS were prepared.
  Interphases comprising PBMCs were collected and transferred to the new centrifuge tubes containing cold PBS.
  For 15 ml tubes interphases from two tubes were collected in one new tube
  For ml tubes interphase from one tube were collected in two new tubes
  A 15 ml centrifuge tube containing cells and PBS was filled up with cold PBS to 15 ml
  The cells were centrifuged for 10 min, at 300 g, 4° C., acceleration: 9, break: 3
  The supernatant was removed and the cells were resuspended in the remaining PBS. Cells from two tubes were collected in one 15 ml centrifuge tube.
  The cells were resuspended in 10 ml cold PBS
  The cells were centrifuged for 10 min, at 300 g, 4° C., acceleration: 9, break: 3
  The supernatant was removed and the cells were resuspended in the remaining PBS. Cells from two tubes were collected in one 15 ml centrifuge tube.
  The cells were resuspended in 10 ml cold PBS
  The cells were centrifuged for 10 min, at 300 g, 4° C., acceleration: 9, break: 3
  The supernatant was removed and the cells were resuspended in the remaining PBS. Cells from all remaining tubes were collected in one 15 ml centrifuge tube.
  The cells were resuspended in 10 ml cold PBS
  The cells were centrifuged for 10 min, at 300 g, 4° C., acceleration: 9, break: 3
  The supernatant was removed and the cells were resuspended in cold PBS
  The cells were counted in a hemocytometer (Dilution: 10 µl cell suspension+10 µl methyl violet+80 µl PBS)
  The cell count was calculated as:
  PBMCs per ml: (Cells counted/number of quadrants)× dilution×$10^4$
  PBMCs total: (Cells counted/number of quadrants)×dilution×$10^4$×cell suspension volume.

3.2 Isolating Monocytes from PBMCs

The isolation of monocytes from PBMCs was performed on the same day as the above described PBMF preparation

3.2.1 Introduction

Monocytes are a type of leukocyte, which can differentiate into macrophages and myeloid dendritic cells. Monocytes constitute 10-30% of all PBMCs and they have a high level of CD14 expression. This protocol describes how monocytes can be isolated from PBMCs with a negative selection procedure, using the monocyte isolation kit II, human, from Miltenyi

3.2.2 Definitions

PBMCs—Peripheral Blood Mononuclear Cells
EDTA—Ethylene-diamine-tetraacetic acid
PBS—Phosphate buffered saline
BSA—Bovine Serum Albumin
Pen/Strep—Penicillin/Streptomycin

3.2.3 Materials

TABLE 3

| Chemicals/Liquids | Manufacture and Cat. No. | Stock Conc. n/Volume |
|---|---|---|
| Monocyte Isolation Kit II, human | Miltenyi, #130-091-153 | — |
| BSA | | |
| EDTA | Amresco, #E177-100 ml | 100 ml |
| PBS | Amresco, #E504-500 ml | 500 ml |
| Trypan blue | BioRad, #1450021 | 0.4% dilution |
| RPMI1640 medium | Invitrogen, #42401018 | 500 ml |
| FBS | Thermo Fisher Scientific, #10270-106 | — |
| Penicillin/Streptomycin | Sigma-Aldrich, #P433 | P: 10,000 U/ml/ S: 10,000 µl/ml |

PBMCs were prepared according to 3.1.

TABLE 4

| Equipment | Manufacture and Cat. No. | Size |
|---|---|---|
| Centrifuge Tube | VWR, #89039-664, #89039-656 | 15 ml, 50 ml |
| Syringe | Braun #4616200V | 20 ml |
| Q-max Syringe Filter | Frisenette # CAPS2502100S | 0.22 µm (pore size) |
| MACS Multistand | Miltenyi, #130-042-303 | — |
| MiniMACS Seperator | Miltenyi, #130-042-102 | Used for MS Columns |
| MidiMACS Seperator | Miltenyi, #130-042-302 | Used for LS Columns |
| LS Column | Miltenyi, #130-042-401 | Capacity: $2 \times 10^9$ cells |

3.2.4. Experimental Procedure

Isolation was performed in accordance with the Miltenyi Monocyte Isolation Kit II, human. Protocol, 1-3, by the following steps in the respective order:
A known amount of PBMCs obtained according to 3.1 was prepared in PBS in a 15 ml centrifuge tube.
Cells were centrifuged for 10 min at 300 g, 4° C., acceleration: 9, break: 3
The supernatant was removed completely and the cells were resuspended in Miltenyi buffer (30 µl per $10^7$ PBMCs).
FcR Blocking Reagent was added (10 µl per $10^7$ PBMCs).
Biotin-Antibody Cocktail was added (10 µl per $10^7$ PBMCs).
The cell suspension was thoroughly resuspended and incubated for 10 min at 4° C.
Miltenyi buffer was added (30 µl per $10^7$ PBMCs).
Anti-Biotin Microbeads were added (20 µl per $10^7$ PBMCs).
Cell suspension was resuspended thoroughly and incubated for 15 min at 4° C.
2 ml miltenyi buffer was added and the cell were resuspended.
The cells were centrifuged for 10 min at 300 g, 4° C., acceleration: 9, break: 3
A MACS separator was placed on a MACS Multistand.
The LS column was placed in the separator and a waste tube was placed under the column.
The column was rinsed with miltenyi buffer (LS: 3000 µl) and collected in the waste tube.
The waste tube was removed and a collecting tube was placed under the column.
The supernatant was completely removed from the centrifuged cells and the cells were resuspended in Miltenyi buffer ($10^8$ cells per 500 µl miltenyi buffer).
The cell suspension was added on top of the column and let sink down.
The column was rinsed 3 times with Miltenyi buffer (LS: 3000 µl per rinse)
The cells were centrifuged for 10 min at 300 g, 4° C., acceleration: 9, break: 3
The supernatant was removed completely and the cells were resuspended in 1 ml warm medium
The cells were counted in a hemocytometer (Dilution: 10 µl cell suspension+10 µl trypan blue+10 µl PBS per $10^7$ PBMCs used)
Cell count was calculated as follows:

$$(\text{Cells counted}/\text{number of quadrants}) \times \text{dilution} \times 10^4$$

3.3 Generating Dendritic Cells from Human Blood Monocytes

The generation of dendritic cells from humane blood monocytes was performed on the same day as monocyte preparation.

3.3.1 Introduction

Figure 3:
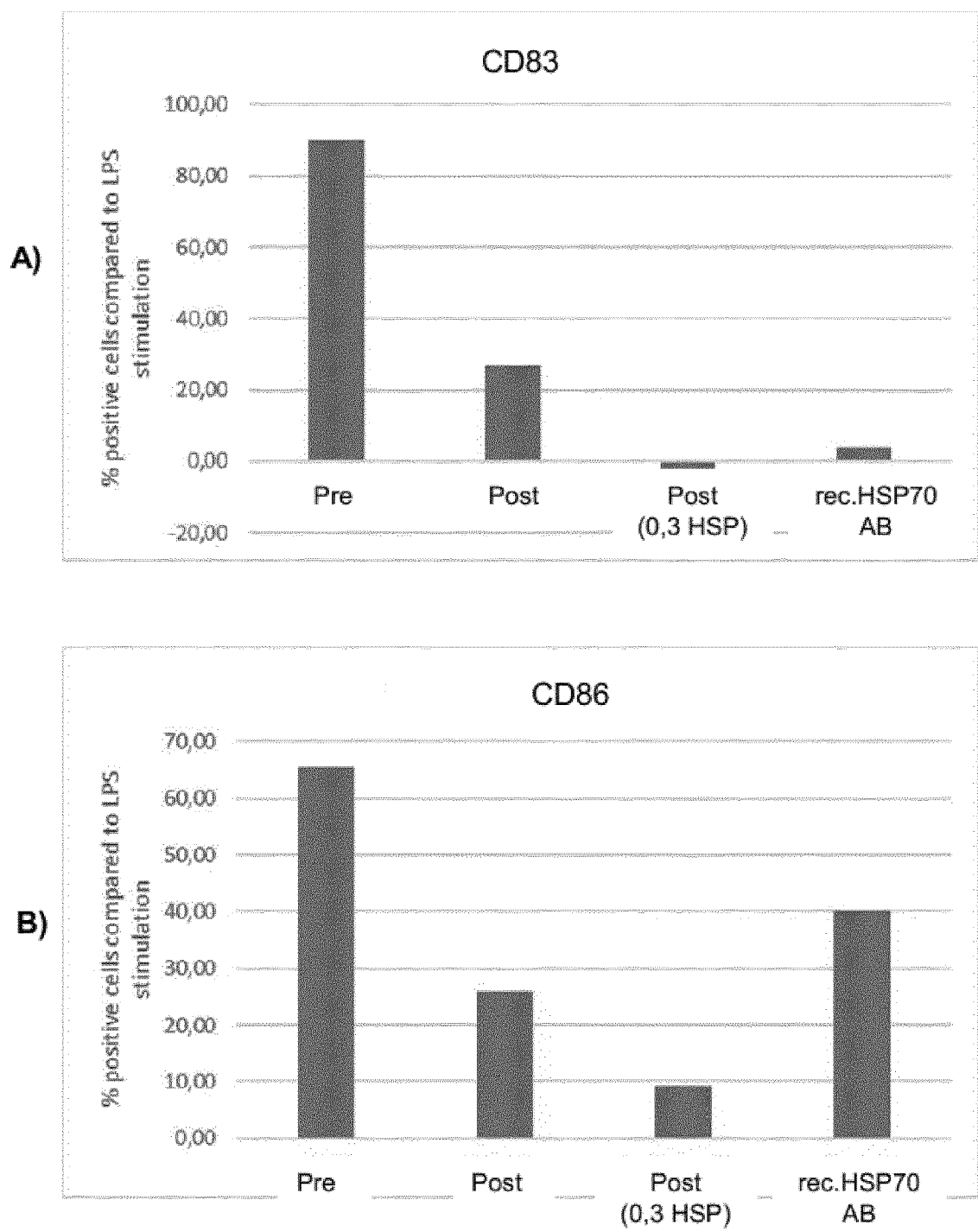
FIG. 3 shows the result for a DC activation and inhibition assay of Example 3 in form of CD83 (FIG. 3A) and CD86 (FIG. 3B) positive DCs in the presence of pre-immune serum (Pre), serum from immunized rat (Post), same with one third of recombinant HSP70 protein (Post (0.3 HSP)) or in the presence of a monoclonal anti-HSP70 antibody (rec. HSP70 AP).

Dendritic cells are antigen presenting cells generating the link between innate and adaptive immunity. These cells constitute only a very small percentage of the cells in the blood and direct isolation of these cells yield a very small number of cells. For in vitro experiments with dendritic cells this creates a problem. Monocytes are a type of leukocyte, which can differentiate into macrophages and myeloid dendritic cells in vivo. Monocytes constitute 10-30% of all PBMCs. These cells are also able to differentiate into dendritic cells in vitro when cultured in medium containing IL-4 and GM-CSF. This protocol describes how to generate dendritic cells from human blood monocytes (FIG. 3).

3.3.2 Definitions

PBMCs—Peripheral Blood Mononuclear Cells
PBS—Phosphate buffered saline
FBS—Fetal Bovine Serum
BSA—Bovine Serum Albumin
IL-4—Interleukine 4
GM-CSF—Granulocyte Macrophage Colony Stimulating Factor
Pen/Strep—Penicillin/Streptomycin
LPS—Lipopolysaccharide

3.3.3 Materials

TABLE 5

| Chemicals/Liquids | Manufacture and Cat. No. | Stock Concentration/Volume |
|---|---|---|
| RPMI1640 medium | Invitrogen, #42401018 | 500 ml |
| FBS | Thermo Fisher Scientific, #10270-106 | — |
| Penicillin/Streptomycin | Sigma-Aldrich, #P433 | P: 10,000 U/ml/ S: 10,000 µl/ml |
| IL-4 | Miltenyi, #130-093-921 | 100 µg/ml |
| GM-CSF | Miltenyi, #130-093-865 | 100 µg/ml |

TABLE 5-continued

| Chemicals/Liquids | Manufacture and Cat. No. | Stock Concentration/ Volume |
|---|---|---|
| LPS | Sigma Aldrich, E. coli #0111:34 | 10 μg/ml |
| Heat Shock Protein 70 Human recombinant | Sigma-Aldrich, #H7283, SLBN9692V | Use Stock 100 μg/mL |
| Anti-HSP70/72 antibody | mAb, mouse IgG1 Enzo, #C92F3A-5 | Use 1:100 |
| 8 rat serum samples | | Use 1:100 and 1:1000 |

Furthermore, freshly isolated monocytes as prepared according to 3.2 were used.

3.3.4 Experimental Procedure for Generation of Immature and Mature DCs

Freshly isolated monocytes obtained according to 3.2 were prepared in warm medium at a density of $1 \times 10^6$ cells/ml.
- The cytokines IL-4 (400 IU/ml) and GM-CSF (1000 IU/ml) were added to the medium.
- Cells were seeded in a well-plate (add only half the medium normally used in the plate. Usual amount of medium in a 12-well plate was 1 ml. 0.5 ml monocyte cell suspension were added. This was done to avoid a total medium exchange on day 3 and instead only fresh medium needs to be added.
- Cells were incubated in a 37° C. $CO_2$ incubator for 3 days
- On day 3 fresh warm medium was added with cytokines IL-4 (400 IU/ml) and GM-CSF (1000 IU/ml), the amount of medium in the well was doubled by this step.
- Cells were incubated in a $CO_2$ incubator for another 3 days.
- On day 6, DCs were stimulated with LPS, human recombinant HSP, and anti-HSP70/72 antibody as follows:
- The total volume of the wells was 300 μl.
- The following mixtures were prepared and added to the wells:

LPS+1:100 Pre-Treatment Serum
1. Mix
   a. 3 μl LPS (10,000 ng/ml) with 3 μl rat pre-treatment serum
2. Incubate for 20-30 min at RT and add to the corresponding wells LPS+1:100 Post-Treatment Serum
1. Mix
   a. 3 μl LPS (10,000 ng/ml) with 3 μl rat post-treatment serum
2. Incubate for 20-30 min at RT and add to the corresponding wells LPS+1:1000 Post-Treatment Serum
1. Mix
   a. 3 μl LPS (10,000 ng/ml) with 0.3 μl rat post-treatment serum
2. Incubate for 20-30 min at RT and add to the corresponding wells Recomb. HSP70 (100 μg/mL)+1:100 Pre-Treatment Serum
1. Mix
   a. 3 μl Recomb. HSP70 with 3 μl rat pre-treatment serum
2. Incubate for 20-30 min at RT and add to the corresponding wells Recomb. HSP70 (100 μg/mL)+1:100 Post-Treatment Serum
1. Mix
   a. 3 μl Recomb. HSP70 with 3 μl rat post-treatment serum
2. Incubate for 20-30 min at RT and add to the corresponding wells Recomb. HSP70 (100 μg/mL)+1:1000 Post-Treatment Serum
1. Mix
   a. 3 μl Recomb. HSP70 with 0.3 μl rat post-treatment serum
2. Incubate for 20-30 min at RT and add to the corresponding wells Prepare the following for the plates:

LPS+1:100 Anti-HSP70/72
1. Mix
   a. 3 μl LPS (10,000 ng/ml) with 3 μl anti-HSP70/72
2. Incubate for 20-30 min at RT and add to the corresponding wells LPS+PBS
1. Mix
   a. 3 μl LPS (10,000 ng/ml) with 3 μl PBS
2. Incubate for 20-30 min at RT and add to the corresponding wells Recomb. HSP70 (100 μg/mL)+1:100 Anti-HSP70/72
1. Mix
   a. 3 μl Recomb. HSP70 with 3 μl anti-HSP70/72
2. Incubate for 20-30 min at RT and add to the corresponding wells Recomb. HSP70 (100 μg/mL)+PBS
1. Mix
   a. 3 μl Recomb. HSP70 with 3 μl PBS
2. Incubate for 20-30 min at RT and add to the corresponding wells The prepared cells for 24 hours in a $CO_2$ incubator

3.4 Flow Cytometry—Harvest, Staining and Analysis

3.4.1 Introduction

Flow cytometry is a laser-based technology used to analyse cells and particles in a suspension. It makes it possible to analyse the size and granularity of the cells and also to detect specific extra- or intracellular molecules, typically by measuring the intensity of fluorescent labelled antibodies.

First we will stain the cells with a viability dye to be able to discriminate between live and dead cells in flow cytometry samples. One type is the protein binding dyes also known as amine-reactive dyes (since they bind to amines) or live/dead fixable dyes. These dyes will bind to proteins and therefore binds both to live and dead cells. However, they function based on the principle that dead cells have compromised membranes, which means the dyes can enter into the intracellular compartment and bind to proteins here giving the dead cells a much higher fluorescence than the live cells. The benefit of these dyes is that once the cells are stained with the viability dyes they can be fixed (they can also be used unfixed) without any reduction in the resolution between live and dead cells. In addition, they are available in a broad range of excitation and emission spectra making them convenient for addition to multi-color flow cytometry panels. This protocol describes how cells are stained with a live/dead staining and stained for maturation markers. We will analyse the maturation of the dendritic cells by targeting the CD83, CD86 and HLA-DR receptors.

3.4.2 Definitions

PBS—Phosphate Buffered Saline
PP Tubes—Polypropylene Tubes

3.4.3 Materials

TABLE 6

| Chemical | Manufacture and Cat. No. | Stock Concentration/Volume |
|---|---|---|
| MilliQ water | Millipore | — |
| 1×PBS | Gibco, # 70011044 | 500 ml |
| SodiumAzide | Sigma Aldrich #26628-22-8 | 1% pre-mixed solution |
| Formaldehyde | Sigma Aldrich, #50-00-0 | 37% solution |
| Fixable Viability Dye Cell Staining eFluor 780 | eBioscience, #65-0865 | — |
| HLA-DR-PE | R&D Systems #FAB4869P-100 | 10 µl in 100 µl |
| CD83-PE-Cy7 | BD Biosciences #561132 | 5 µl in 100 µl |
| CD86-BV421 | BD Biosciences #562432 | 5 µl in 100 µl |
| Isotype, IgG1, κ, PE | | 10 µl in 100 µl |
| Isotype, IgG1, κ, PE-Cy7 | | 5 µl in 100 µl |
| Isotype, IgG1, κ, BV421 | | 5 µl in 100 µl |

TABLE 7

| Equipment | Manufacture and Cat. No. | Size |
|---|---|---|
| Centrifuge Tube | VWR, #89039-664, #89039-656 | 15 ml, 50 ml |
| Syringe | Braun #4616200V | 20 ml |
| Q-max Syringe Filter | Frisenette # CAPS2502100S | 0.22 µm (pore size) |
| Blue Cap bottle | — | 50-200 ml |
| PP tubes | VWR, # | 5 ml |

TABLE 8

| DC Maturation panel | | | |
|---|---|---|---|
| Antibody | Volume | Isotype | Volume |
| HLA-DR-PE RND Systems # FAB4869P-100 | 10 µl | IgG1, κ, PE | 10 µl |
| CD83-PE-Cy7 BD# 561132 | 5 µl | IgG1, κ, PE-Cy7 | 5 µl |
| CD86-BV421 BD # 562432 | 5 µl | IgG1, κ, BV421 | 5 µl |

Flow buffer:
PBS
0.1% BSA
0.01% sodium azide
The solution was mixed in a bluecap bottle and prepared a syringe with a 0.22 µm sterile filter and run the solution through the filter collecting it in a new bluecap bottle.
Stored at 4° C.
Fixation buffer:
PBS
1% formaldehyde
Stored at 4° C.

3.4.4 Experimental Procedure

Cells were harvested from the wells prepared according to 3.3 by flushing them in the media and transferred to the corresponding PP tube.
The procedure was repeated by adding 500 µl cold PBS to each well, flushing them in the media and transferred to the corresponding PP tube. Transfer 50 µl from each tube to a PP tube marked "Isotypes" and transfer 50 µl of each type to a PP tube marked "unstained"
The cells were centrifuged at 300 g, 4° C., for 5 min, acc. 9, break 3
The supernatant was removed and discarded it in a waste tube
The cells were vortexed briefly
The Fixable Viability Dye Cell Staining eFluor 780 1:1000 was mixed in 1×PBS (Fx. 1 µl Dye to 999 µl 1×PBS).
0.5 ml of said mix was added to each tube and cells were incubated at 4° C. in the dark for 30 min.
2 ml 1×PBS was added to each tube and resuspend the cells.
Cells were centrifuged at 300 g, 4° C., for 5 min, acc. 9, break 3
Supernatant was removes and discard it in a waste tube
2 ml flow buffer were added to each tube and cells were resuspended therein
Cells were centrifuged at 300 g, 4° C., for 5 min, acc. 9, break 3
Supernatant was removes and discard it in a waste tube
The cells were vortexed briefly
A master mix of the antibodies comprising:
Fx. 20 tubes=200 µl HLA-DR-PE+100 µl PE-Cy7+100 µl BV421 was prepared
20 µl of a master mix comprising 200 µl HLA-DR-PE+ 100 µl PE-Cy7+100 µl BV421 was added to each PP tube and further 10 µl isotype PE+5 µl isotype PE-Cy7+5 µl BV421 were added to the isotype samples but not to the control samples.
Tubes were incubated at 4° C. in the dark for 30 min
2 ml flow buffer were added to each tube and the cells were resuspended therein.
Cells were centrifuged at 300 g, 4° C., for 5 min, acc. 9, break 3
200 µl HLA-DR-PE+100 µl PE-Cy7+100 µl BV421Add 2 ml flow buffer was added to each tube and cells were resuspended.
Cells were centrifuged at 300 g, 4° C., for 5 min, acc. 9, break 3
Supernatant was removes and discard it in a waste tube
Perform the following in the flow bench:
Under a flow bench, the cells were fixated by adding 100 µl fixation buffer to each tube and mixing by pipetting up and down 5-10 times.
Samples were placed in the refrigerator overnight.
On the next day, the samples were transferred to a 96-well plate with V-bottom in a Flow-lab under a local exhaust ventilation.
Finally, the cells were counted in a flow cytometer. Respective settings are show in FIG. 3.

TABLE 9

| DC Maturation panel: | | | |
|---|---|---|---|
| Antibody | Volume | Isotype | Volume |
| HLA-DR-PE RND Systems # FAB4869P-100 | 10 µl | IgG1, κ, PE | 10 µl |
| CD83-PE-Cy7 BD # 561132 | 5 µl | IgG1, κ, PE-Cy7 | 5 µl |
| CD86-BV421 BD # 562432 | 5 µl | IgG1, κ, BV421 | 5 µl |

3.5 Results

FIG. 3 shows the result for DC activation and inhibition as represented by the number of CD83 (A) and CD86 (B) positive dendritic cells. In the presence of pre-immune serum (Pre), dendritic cells were fully activated by LPS. Upon addition of serum obtained from immunized rat no. 2 (Post), a significant inhibition of DC activation could be observed. This inhibition was increased when only one third of recombinant Hsp70 was used in the activation assay (Post (0,3 HSP)). As expected for the positive inhibition control, also the recombinant anti-Hsp70 antibody (rec. HSP70 AP) significantly inhibited the DC activation.

The results confirm that AAVLP-HSP70i according to the invention in vivo induced antibodies that are suitable for inhibiting DC activation. Thus, it can be concluded that administration of AAVLP-HSP70i according to the invention will be able to significantly inhibit HSP70i driven DC activation. Accordingly, these data establish a proof of concept for treating autoimmune diseases by AAVLP-HSP70i administration according to the invention.

Example 4: In Vivo Vitiligo-Model

4.1 Methods

To evaluate the efficacy of the AAVLP-HSP70i vaccines in vivo, a vitiligo-prone mice model that develops spontaneous epidermal depigmentation from 4 weeks of age was used. These h3TA2 transgenic mice expresses both a human-derived, tyrosinase-reactive T-cell receptor (TCR) on T cells and the matching HLA-A2 transgenes recognizing melanocytes (Eby et al. 2014; Mehrotra et al. 2012). The mice were from 5 week of age subcutaneous (s.c.) injected twice with a 2-week interval with the AAVLP-HSP70i_Q435A_453 obtained as described above (1.5 mg/mL, 0.1 mL per inject., n=7). As a negative control mice were s.c. injected with AAVLPs comprising an HPV epitope insert as disclosed in WO2012031760 A1 (83 µg/mL, 0.1 mL per injection, n=5). Depigmentation was documented from 5 weeks of age with a 2-week interval until 11 weeks of age using a flatbed scanner (Hewlett-Packard Company, Palo Alto, Calif.) and Adobe Software (Adobe Systems, Inc., San Jose, Calif.), Depigmentation was calculated as descried previously by Denman et al. (2008). Briefly, anesthetized mice were placed on a flatbed scanner and resulting images were subjected to image analysis using Adobe Photoshop. Depigmentation was calculated from the largest evaluable area as the percentage of pixels among >150,000 evaluated with a luminosity above the cut-off level set to include 95% of pixels for untreated mice. Statistical analysis of data was analyzed by repeated measure two-way ANOVA with Sidak's multiple comparisons test. All statistics were performed using Graph Pad Prism software. Data are presented as mean±SD and P values of 0.05 were considered significant. The depigmentation established at 5 weeks of age (time point of 1st vaccination) is set to 1. The average fold change of depigmentation is calculated relative to the depigmentation at 5 weeks of age and averaged over the mice in each group.

4.2 Results

Figure 5:
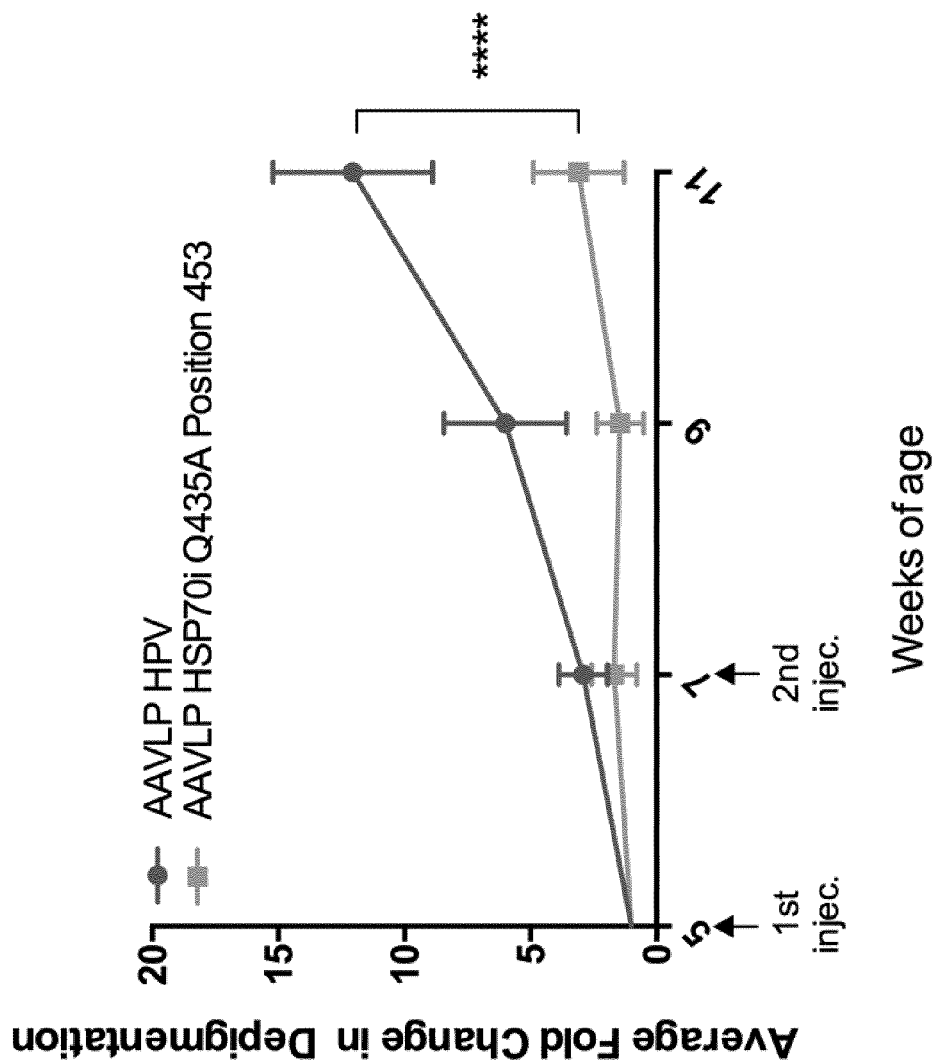
FIG. 5 shows the result of a vitiligo in vivo mouse model. Change of depigmentation in mice immunised with AAVLP-HSP70i_Q435A_453 in comparison to control (AAVLP-HPV) is shown.

The average fold change in depigmentation of the ventral side of the mice is shown in FIG. 5. The results demonstrate a string inhibition of depigmentation by AAVLP-HSP70i_Q435A in comparison to the AAVLP-HPV control. The results establish the in vivo proof of concept of the invention described herein.

REFERENCES

Denman C J, McCracken J, Hariharan V, Klarquist J, Oyarbide-Valencia K, Guevara-Patiño J A, Le Poole I C. (2008) HSP70i accelerates depigmentation in a mouse model of autoimmune vitiligo. J Invest Dermatol. 128(8): 2041-8.

Eby J M, Kang H K, Klarquist J, Chatterjee S, Mosenson J A, Nishimura M I, Garrett-Mayer E, Longley B J, Engelhard V H, Mehrotra S, Le Poole I C. (2014) Immune responses in a mouse model of vitiligo with spontaneous epidermal de- and repigmentation. Pigment Cell Melanoma Res. 27(6):1075-85

Frietze K M, Peabody D S, Chackerian B. (2016) Engineering virus-like particles as vaccine platforms. Curr Opin Virol. 18:44-49

Jacquemin C, Rambert J2, Guillet S, Thiolat D, Boukhedouni N, Doutre M S, Darrigade A S, Ezzedine K, Blanco P5 Taieb A, Boniface K, Seneschal J. (2017) HSP70 potentiates interferon-alpha production by plasmacytoid dendritic cells: relevance for cutaneous lupus and vitiligo pathogenesis. Br J Dermatol. doi: 10.1111/bjd.15550

King J A, Dubielzig R, Grimm D, Kleinschmidt J A. (2001) DNA helicase-mediated packaging of adeno-associated virus type 2 genomes into preformed capsids. Embo J. 20: 3282-91.

Malyshev I (2013) Immunity, Tumors and Aging: The Role of HSP70. Dordrecht, Heidelberg, New York, London: Springer. 63-82

Mansilla M J, Montalban X, Espejo C. (2012) Heat shock protein 70: roles in multiple sclerosis Mol Med. 18:1018-28

Mehrotra S, Al-Khami A A, Klarquist J, Husain S, Naga O, Eby J M, Murali A K, Lyons G E, Li M, Spivey N D, Norell H, Martins da Palma T, Onicescu G, Diaz-Montero C M, Garrett-Mayer E, Cole D J, Le Poole I C, Nishimura M I. (2012) A coreceptor-independent transgenic human TCR mediates anti-tumor and anti-self immunity in mice. J Immunol. 189(4):1627-38

Millar D G, Garza K M, Odermatt B, Elford A R, Ono N, Li Z, Ohashi P S. (2003) Hsp70 promotes antigen-presenting cell function and converts T-cell tolerance to autoimmunity in vivo. Nat Med. 9(12):1469-76

Mosenson J A, Zloza A, Nieland J D, Garrett-Mayer E, Eby J M, Huelsmann E J, Kumar P, Denman C J, Lacek A T, Kohlhapp F J, Alamiri A, Hughes T, Bines S D, Kaufman H L, Overbeck A, Mehrotra S, Hernandez C, Nishimura M I, Guevara-Patino J A, Le Poole I C. (2013) Mutant HSP70 reverses autoimmune depigmentation in vitiligo. Sci Transl Med. 5(174):174ra28

Mosenson J A, Flood K, Klarquist J, Eby J M, Koshoffer A, Boissy R E, Overbeck A, Tung R C, Le Poole I C. (2014) Preferential secretion of inducible HSP70 by vitiligo melanocytes under stress. Pigment Cell Melanoma Res. 27(2): 209-20

Sonntag F, Schmidt K, Kleinschmidt J A. (2010) A viral assembly factor promotes AAV2 capsid formation in the nucleolus. Proc Natl Acad Sci USA. 107(22):10220-5

Speeckaert R, van Geel N. (2017) Vitiligo: An Update on Pathophysiology and Treatment Options. Am J Clin Dermatol. doi: 10.1007/s40257-017-0298-5. PMID: 28577207

Wang D, Eiz-Vesper B, Zeitvogel J, Dressel R, Werfel T, Wittmann M.(2011) Human keratinocytes release high levels of inducible heat shock protein 70 that enhances peptide uptake. Exp Dermatol. 20(8):637-41

The invention claimed is:

1. A mutated parvovirus structural protein, comprising at least one insertion comprising a sequence of at least six consecutive amino acids comprised within amino acids 320 to 641 of human HSP70i.

2. The mutated parvovirus structural protein according to claim 1, wherein the amino acid sequence comprised in the insertion comprises an amino acid sequence which is involved in the activation of antigen-presenting cells by HSP70i.

3. The mutated parvovirus structural protein according to claim 1, wherein the amino acid sequence of the insertion comprises at least one mutation in comparison to a corresponding sequence in HSP70i.

4. The mutated parvovirus structural protein according to claim 1, wherein the amino acid sequence of the insertion comprises the amino acid sequence APGVLIQVYEG (SEQ ID NO:4) and/or QPGVLIQVYEG (SEQ ID NO:2).

5. The mutated parvovirus structural protein according to claim 1, wherein the mutated parvovirus structural protein is derived from AAV.

6. The mutated parvovirus structural protein according to claim 1, wherein the mutated parvovirus structural protein is a mutated VP3 protein.

7. The mutated parvovirus structural protein according to claim 1, wherein the mutated parvovirus structural protein comprises two or more insertions.

8. The mutated parvovirus structural protein according to claim 1, wherein the insertions are at positions I-587 and/or I-453.

9. The mutated parvovirus structural protein according to claim 1, wherein the mutated parvovirus structural protein comprises a linker sequence, and/or comprises one or more additional mutations selected from an insertion, a deletion, a N- or C-terminal fusion of a heterologous amino acid sequence and a substitution.

10. A multimeric structure, wherein the multimeric structure is a virus-like particle comprising a mutated parvovirus structural protein according to claim 1.

11. A nucleic acid encoding the mutated parvovirus structural protein according to claim 1.

12. A composition comprising the mutated parvovirus structural protein according to claim 1 for use as medicament.

13. The composition according to claim 12, wherein the medicament is a vaccine.

14. The composition according to claim 12, wherein the medicament is for use in a method for treating or preventing an autoimmune and/or inflammatory disease or in a method of immunosuppression.

15. The composition according to claim 14, wherein the autoimmune and/or inflammatory disease is selected from vitiligo, alopecia, arthritis, psoriasis, lupus erythematosus, multiple sclerosis, Parkinson's disease, autoimmune diabetes, graft versus host disease, Neuromyelitis optica (NMO), Acute optic neuritis (AON), oophorytis, and tumors expressing HSP70.

16. The composition according to claim 13, wherein the vaccine is for use in a method for treating or preventing an autoimmune and/or inflammatory disease or in a method of immunosuppression.

17. The mutated parvovirus structural protein according to claim 5, wherein the AAV protein is AAV2.

18. The composition according to claim 15, wherein the arthritis is rheumatoid arthritis.

* * * * *

SEQUENCE LISTING

<160> NUMBER OF SEQ ID NOS: 5

<210> SEQ ID NO 1
<211> LENGTH: 641
<212> TYPE: PRT
<213> ORGANISM: Homo sapiens
<220> FEATURE:
<223> OTHER INFORMATION: equivalent to the sequence of Gene Bank accession no. AQY76873.1

<400> SEQUENCE: 1

```
Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Asp Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350
```

```
Phe Phe Asn Gly Arg Asp Leu Asn Lys Ser Ile Asn Pro Asp Glu Ala
            355                 360                 365
Val Ala Tyr Gly Ala Ala Val Gln Ala Ala Ile Leu Met Gly Asp Lys
        370                 375                 380
Ser Glu Asn Val Gln Asp Leu Leu Leu Asp Val Ala Pro Leu Ser
385                 390                 395                 400
Leu Gly Leu Glu Thr Ala Gly Gly Val Met Thr Ala Leu Ile Lys Arg
                    405                 410                 415
Asn Ser Thr Ile Pro Thr Lys Gln Thr Gln Ile Phe Thr Thr Tyr Ser
                420                 425                 430
Asp Asn Gln Pro Gly Val Leu Ile Gln Val Tyr Glu Gly Glu Arg Ala
                435                 440                 445
Met Thr Lys Asp Asn Asn Leu Leu Gly Arg Phe Glu Leu Ser Gly Ile
        450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Thr Ala Thr Asp Lys Ser Thr Gly
                    485                 490                 495
Lys Ala Asn Lys Ile Thr Ile Thr Asn Asp Lys Gly Arg Leu Ser Lys
                500                 505                 510
Glu Glu Ile Glu Arg Met Val Gln Glu Ala Glu Lys Tyr Lys Ala Glu
            515                 520                 525
Asp Glu Val Gln Arg Glu Arg Val Ser Ala Lys Asn Ala Leu Glu Ser
530                 535                 540
Tyr Ala Phe Asn Met Lys Ser Ala Val Glu Asp Glu Gly Leu Lys Gly
545                 550                 555                 560
Lys Ile Ser Glu Ala Asp Lys Lys Lys Val Leu Asp Lys Cys Gln Glu
                565                 570                 575
Val Ile Ser Trp Leu Asp Ala Asn Thr Leu Ala Glu Lys Asp Glu Phe
                580                 585                 590
Glu His Lys Arg Lys Glu Leu Glu Gln Val Cys Asn Pro Ile Ile Ser
            595                 600                 605
Gly Leu Tyr Gln Gly Ala Gly Gly Pro Gly Pro Gly Gly Phe Gly Ala
        610                 615                 620
Gln Gly Pro Lys Gly Gly Ser Gly Ser Gly Pro Thr Ile Glu Glu Val
625                 630                 635                 640
Asp

<210> SEQ ID NO 2
<211> LENGTH: 11
<212> TYPE: PRT
<213> ORGANISM: Homo sapiens

<400> SEQUENCE: 2

Gln Pro Gly Val Leu Ile Gln Val Tyr Glu Gly
1               5                   10

<210> SEQ ID NO 3
<211> LENGTH: 21
<212> TYPE: PRT
<213> ORGANISM: Homo sapiens
```

-continued

```
<400> SEQUENCE: 3

Thr Tyr Ser Asp Asn Gln Pro Gly Val Leu Ile Gln Val Tyr Glu Gly
1               5                   10                  15

Glu Arg Ala Met Thr
            20

<210> SEQ ID NO 4
<211> LENGTH: 11
<212> TYPE: PRT
<213> ORGANISM: Artificial Sequence
<220> FEATURE:
<223> OTHER INFORMATION: amino acids 435 to 445 with Q435A mutation

<400> SEQUENCE: 4

Ala Pro Gly Val Leu Ile Gln Val Tyr Glu Gly
1               5                   10

<210> SEQ ID NO 5
<211> LENGTH: 21
<212> TYPE: PRT
<213> ORGANISM: Artificial Sequence
<220> FEATURE:
<223> OTHER INFORMATION: amino acids 430 to 450 with Q435 mutation

<400> SEQUENCE: 5

Thr Tyr Ser Asp Asn Ala Pro Gly Val Leu Ile Gln Val Tyr Glu Gly
1               5                   10                  15

Glu Arg Ala Met Thr
            20
```